United States Patent [19]
Adam et al.

[11] Patent Number: 6,107,342
[45] Date of Patent: Aug. 22, 2000

[54] 2-AMINO-BICYCLO[3.1.0]HEXANE-2,6-DICARBOXYLIC ACID DERIVATIVES AND A PROCESS FOR THE PREPARATION THEREOF

[75] Inventors: Geo Adam, Schopfheim, Germany; Philippe Nicolas Huguenin-Virchaux, Liestal, Switzerland; Vincent Mutel, Mulhouse, France; Heinz Stadler, Rheinfelden, Switzerland; Thomas Johannes Woltering, Weil am Rhein, Germany

[73] Assignee: Hoffmann-La Roche Inc., Nutley, N.J.

[21] Appl. No.: 09/385,935

[22] Filed: Aug. 30, 1999

[30] Foreign Application Priority Data

Sep. 3, 1998 [EP] European Pat. Off. ............. 98116670

[51] Int. Cl.$^7$ ...................... A61K 31/195; C07C 61/28; C07C 247/00
[52] U.S. Cl. ........................... 514/561; 514/566; 552/11; 552/12; 562/501
[58] Field of Search ................................... 514/561, 566; 562/501; 552/11, 12

[56] References Cited

U.S. PATENT DOCUMENTS 5,321,143  6/1994  Sharpless et al. .

FOREIGN PATENT DOCUMENTS 0 751 117  1/1996  European Pat. Off. .
0 774 455  5/1997  European Pat. Off. .

OTHER PUBLICATIONS

Godjoian et al., American Chemical Society, Symposium Series (Reductions in Organic Synthesis), vol. 641, chapter 10, p. 153–166 (1996).
Sarma et al., Chemistry & Industry (London), No. 21, p. 764 (Nov. 2, 1987).
Gao et al., J. Am. Chem. Soc., vol. 110, No. 22, p. 7538–7539 (1988).
Baldwin et al., J. Chem. Soc., Chem. Commun., p. 409–411 (1986).
Rosen et al., J. Org. Chem., vol. 53, p. 1580–1582 (1988).
Thompson et al., J. Org. Chem., vol. 57, No. 22, p. 5979–5989 (1992).
Shao et al., J. Org. Chem., vol. 61, No. 8, p. 2582–2583 (1996).
Schaffhauser et al., Molecular Pharmacology, vol. 53, 228–233 (1998).
Organic Syntheses, Ed. Baumgarten, H.E. et al., Collective vol. 5, 586–589 (1973).
Larock, Comprehensive Organic Transformations: A Guide to Functional Group Preparations, pp. 527–528, 360–362, 604–614 (1989).
Kolb, et al., Tetrahedron:Asymmetry, vol. 4, No. 1, p. 133–141 (1993).

Primary Examiner—Gary Geist
Assistant Examiner—Leigh C. Maier
Attorney, Agent, or Firm—George W. Johnson; Patricia S. Rocha-Tramaloni; Eileen M. Ebel

[57] ABSTRACT

The present invention relates to the compound of formulae

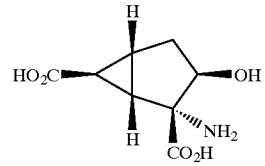

I-A

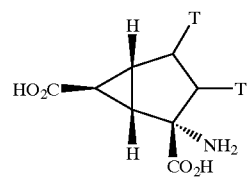

I-B

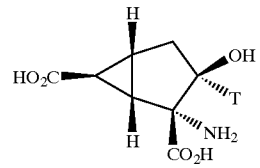

I-C and to a process for the manufacture of compounds of the general formula

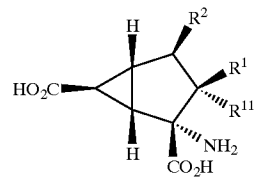

I which are ligands for the metabotropic glutamate receptors of group II, wherein T is tritium;
$R^1$ is hydroxy, lower alkoxy, lower alkenyloxy, benzyloxy, hydrogen, deuterium or tritium;
$R^{11}$ is hydrogen, deuterium or tritium, hydroxy or amino, and
$R^2$ is hydrogen or tritium, or
$R^1$ and $R^2$ form a bond.

18 Claims, No Drawings

2-AMINO-BICYCLO[3.1.0]HEXANE-2,6-DICARBOXYLIC ACID DERIVATIVES AND A PROCESS FOR THE PREPARATION THEREOF

FIELD OF THE INVENTION

The present invention relates to ligands for the metabotropic glutamate receptors of Group II and methods for making the ligands.

BACKGROUND OF THE INVENTION

In the central nervous system (CNS) the transmission of stimuli takes place by the interaction of a neurotransmitter, which is sent out by a neuron, with a neuroreceptor. L-glutamic acid, the most commonly occurring neurotransmitter in the CNS, plays a critical role in a large number of physiological processes. The glutamate-dependent stimulus receptors are divided into two main groups. The first main group forms ligand-controlled ion channels. The metabotropic glutamate receptors (mGluR) belong to the second main group and, furthermore, belong to the family of G-protein-coupled receptors.

At present, eight different members of these mGluRs are known and of these some even have sub-types. On the basis of structural parameters, the different second messenger signaling pathways and the different affinities to low-molecular weight chemical compounds, these eight receptors can be sub-divided into three sub-groups: mGlu1 and mGlu5 belong to group I, mGlu2 and mGlu3 belong to group II and mGlu4, mGlu6, mGlu7 and mGlu8 belong to group III.

Generally, these receptors function to modulate the presynaptic release of glutamate, and the postsynaptic sensitivity of the neuronal cell to glutamate excitation. The metabotropic glutamate receptors are useful targets for the treatment of acute and chronic neurological conditions and psychiatric disorders.

Ligands for the metabotropic glutamate receptors are described, for example, in EP 774 455. Compounds described therein are useful as modulators of metabotropic glutamate receptor function. These compounds differ from compounds of the present formula I by one or two substitutions on the ring molecule. The syntheses described for generically encompassed compounds are very uncertain and vague, and they lead to mixtures of diastereomers and/or enantiomers which would have to be separated into dean isomers by tedious and time-consuming procedures.

SUMMARY OF THE INVENTION

The present invention provides a process for the preparation of a compound of formula

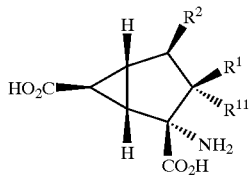

I wherein
$R^1$ is hydroxy, lower alkoxy, lower alkenyloxy, benzyloxy, hydrogen, deuterium or tritium,
$R^{11}$ is hydrogen, deuterium, tritium, hydroxy or amino, and $R^2$ is hydrogen or tritium, or
$R^1$ and $R^2$ form a bond,
which process comprises:
a) reacting a compound of formula

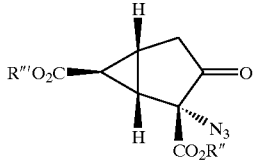

IX with a reducing agent, to obtain a compound of formula VII and a compound of formula X

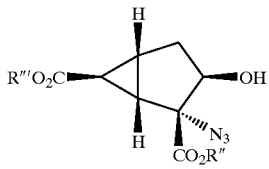

VII

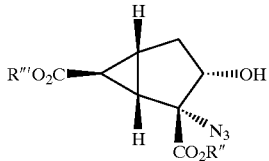

X wherein R'" and R" are each independently selected from benzyl or lower alkyl, and then, starting with either or both the compounds of formula VII and X,
b) reacting with a reducing agent to reduce the azide group, and
c) hydrolyzing the ester groups,
to obtain a compound of formula I.

The process of producing a compound of formula I according to the present invention can also include, after step a):
d) reacting either or both the compound of formula VII or X with trifluoromethane sulfonic acid anhydride to obtain a resultant, and then
e) reacting the resultant of step d) in a base to obtain a compound of formula XXVI

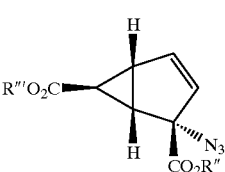

XXVI and
f) treating with a gas selected from the group consisting of hydrogen and tritium gas and a mixtures thereof.

The process of producing a compound of formula I according to the present invention can alternatively include, after step a):
g) reacting either or both the compound of formula VII or X with trifluoromethane sulfonic acid anhydride to obtain a resultant, and then h) reacting the resultant of step g) with a reagent having an azide group in a polar, aprotic solvent, to obtain a compound of formula XXVIII

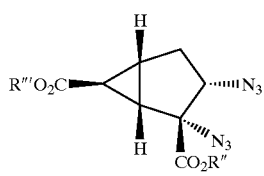

XXVIII

The process of producing a compound of formula I according to the present invention can alternatively include, after step a):

i) alkylating, alkenylating or benzylating either or both the compound of formula VII or X.

The present invention also provides compounds of formulae

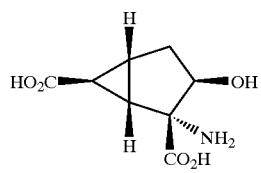

I-A

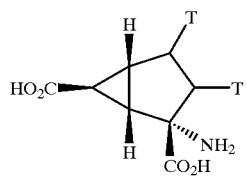

I-B

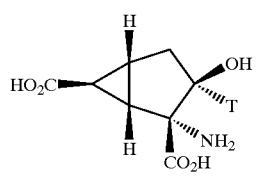

I-C and

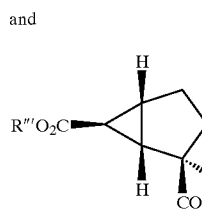

VII in which R″ and R‴ are each independently selected from benzyl or lower alkyl and wherein compounds of formula VII and intermediates for the preparation of formula I compounds.

The present invention further provides a method of controlling or preventing neurological diseases or psychiatric disorders comprising administering to a patient in need of treatment an effective amount of the compound of formula I-A. An effective dose is, for example, from about 1 mg to about 1000 mg per day for an average patient weighing 70 kg.

DETAILED DESCRIPTION OF THE INVENTION

The Present invention is directed to compounds of formulae

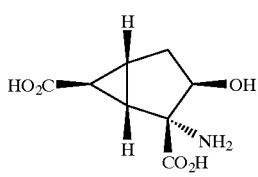

I-A

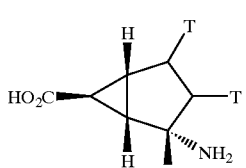

I-B

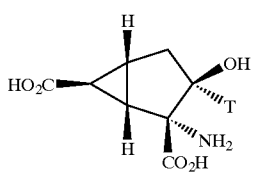

I-C and to a process for the manufacture of compounds of the general formula

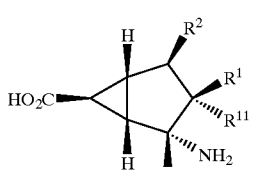

I wherein

T is tritium;

$R^1$ is hydroxy, lower alkoxy, lower alkenyloxy, benzyloxy, hydrogen, deuterium or tritium;

$R^{11}$ is hydrogen, deuterium or optionally tritium, hydroxy or amino and $R^2$ is hydrogen or optionally tritium or $R^1$ and $R^2$ form a bond.

Compounds of general formula I are ligands for the metabotropic glutamate receptors of group II.

It has now surprisingly been found that compounds of the general formula I can be prepared in high yield and in high diastereoisomeric and enantiomeric purity in a new synthetic way.

The following definitions of the general terms used in the present description apply irrespective of whether the terms in question appear alone or in combination.

As used herein, the term "lower alkyl" denotes a straight- or branched-chain alkyl group containing from 1–6 carbon atoms, for example, methyl, ethyl, propyl, i-propyl, n-butyl, i-butyl, t-butyl, pentyl or hexyl.

Also, the term "lower alkenyl" denotes the same kind of straight- or branched-chain moiety as described with "lower alkyl", but containing multiple bond(s).

The term "leaving group" means, for example, an iodide-, bromide-, chloride-, methanesulfonate-, tolylsulfonate- or trifluoromethanesulfonate-group.

The term "halogen" denotes chlorine, iodine, fluorine or bromine.

The present invention also provides compounds of formulae

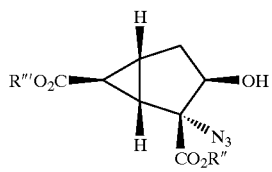
VII in which R″ and R′″ are independently from each other benzyl or lower alkyl, wherein compounds of formula VII are used as intermediates for the process for preparation of compounds of formulae I-A and I.

In accordance with the present invention, compounds of formula I-A are used for the control or prevention of acute and chronic neurological conditions and psychiatric disorders. In accordance with the present invention, compounds of formulae I-B and I-C can be used as radio ligands in a binding assay in order to screen chemical libraries to identify further structures of potential interest.

In accordance with the present invention, the process comprises

A) reducing the carbonyl group of a compound of formula

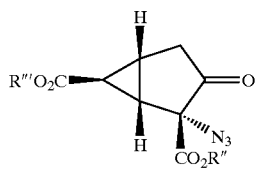
IX to a hydroxy group of a compound of formula VII and formula X

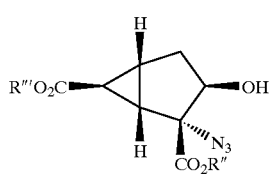
VII

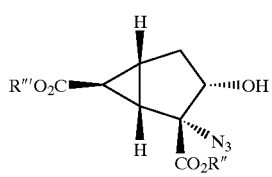
X wherein R′″ and R″ are independently from each other benzyl or lower alkyl, and, if desired, B) i) replacing the hydroxy group of a compound of formula VII or X with a leaving group, and
ii) eliminating the leaving group to obtain a compound of formula XXVI, or
iii) substituting said leaving group with azide to obtain a compound of formula XXVIII,

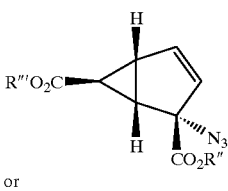
XXVI or

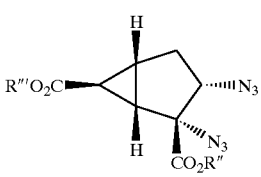
XXVIII and if desired,

C) alkylating, alkenylating or benzylating a compound of formula VII or X and

D) reducing the azide group(s) into (an) amino group(s), for example, reducing the azide group of formula XXVI to obtain a compound of formula XXVII, or reducing the azide groups of formula XXVIII to obtain a compound of formula XXIX,

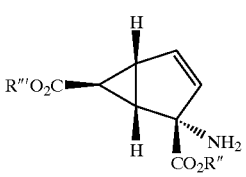
XXVII or

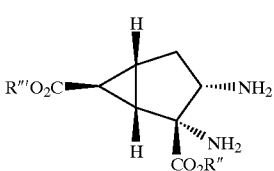
XXIX and

E) hydrolyzing the ester groups, for example, hydrolyzing the ester groups of the compound of formula XXVII or XXIX to a compound of formula I-10 or to a compound of formula I-12, respectively

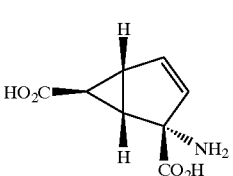
I-10 or

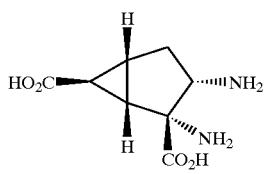

I-12 and

F) where a compound having ring with a double bond results, for example, a compound of formula XXVI or I-10, hydrogenating the double bond with hydrogen, tritium or hydrogen and tritium gas.

Enantiomeric selectivity is achieved, for example, in step b)iii), in which a compound of formula XXVIII results.

In the following schemes 1–5 are described the processes for preparation of the starting compound of formula VII to compounds of formulae I-A, I-B, and I-C and processes for preparation of compounds of formula I.

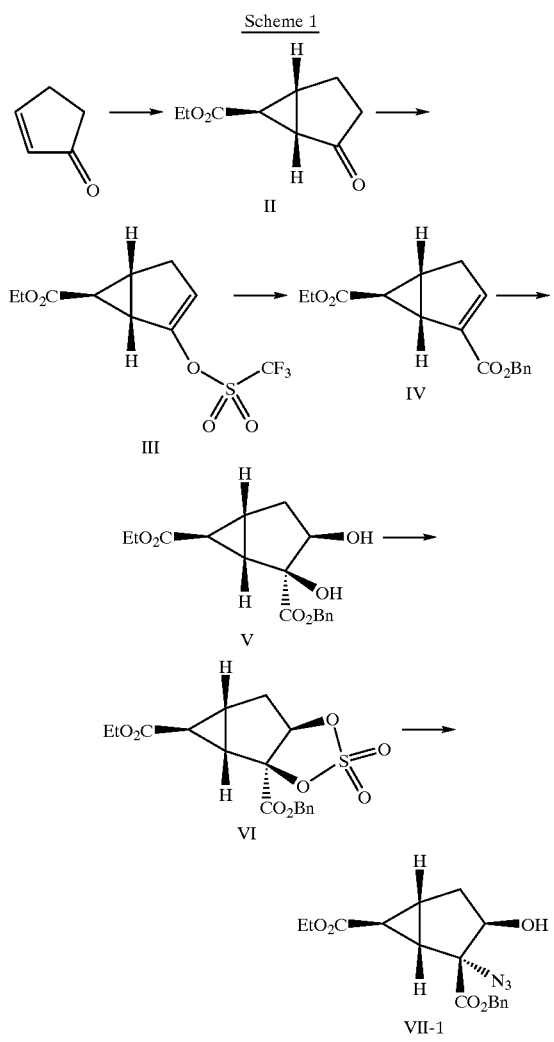

Scheme 1

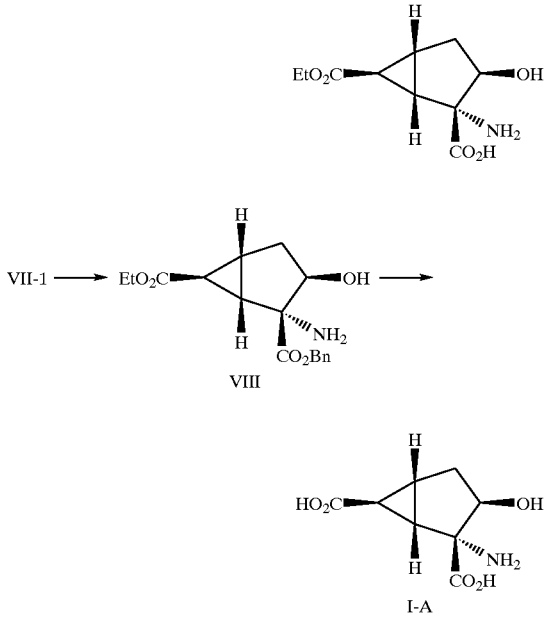

wherein Bn is benzyl.

According to scheme 1, compounds of general formula VII can be prepared from compounds of general formula

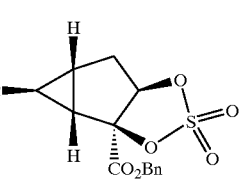

VI by reacting with an azide, preferably sodium azide in a polar, aprotic solvent, like for example dimethylformamide (DMF), at temperatures of around 100° C. or in aqueous solutions of water-miscible solvents, like for example acetone or tetrahydrofuran, at temperatures around 50° C. and then hydrolyzing the formed sulfate half ester with an acid, preferably sulfuric acid.

An example for this kind of transformation can be found in *J. Am. Chem. Soc.* 1988, 110 (22), 7538.

Compounds of general formula VI can be prepared by reacting compounds of general formula V

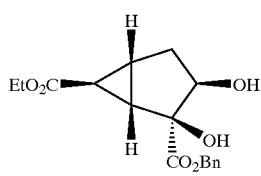

V with thionyl chloride in an aprotic solvent to yield a cyclic sulfite. If desired, the reaction can be carried out in the presence of a base. Then the cyclic sulfite is oxidized to the cyclic sulfate. Suitable solvents for the formation of the sulfite are, for example, chlorinated solvents such as dichloromethane, chloroform, carbon tetrachloride or dichloroethane. Suitable bases can be selected from amines, for example, but not limited to, triethylamine or diisopropylethylamine. A preferred oxidant is, for example sodiumperiodate in the presence of catalytic amounts of a ruthenium salt, such as ruthenium trichloride. The oxidation is preferably carried out in a solvent mixture consisting of carbon tetrachloride, acetonitrile and water in a ratio of from about 1:1:1 to about 2:2:3.

A procedure for the preparation of cyclic sulfates can be found in U.S. Pat. No. 5,321,143.

Compounds of general formula V can be prepared by performing an asymmetric cishydroxylation (Sharpless AD) reaction on compounds of general formula

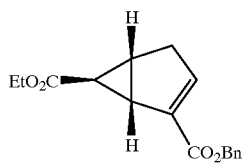

IV

This reaction allows for the selective preparation of one desired isomer of compounds of general formula V out of four possible isomers (two diastereoisomeric pairs of enantiomers). Examples for the use of the asymmetric cis-hydroxylation reaction can be found in for example *J. Org. Chem.* 1996, 61(8), 2582–2583 and *Tetrahedron:Asymmetry* 1993, 4(1), 133–141.

Compounds of general formula IV can be prepared from compounds of general formula

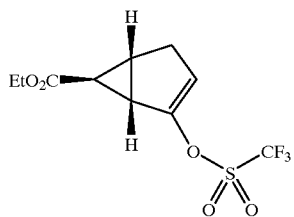

III by a transition metal catalyzed carbon monoxide insertion in the presence of the alcohol

R'''—OH.

wherein R''' is benzyl or lower alkyl,

The reaction can be carried out in R'''—OH as the solvent or aprotic solvents such as, for example tetrahydrofuran or DMF with stochiometric amounts (one to two equivalents) of R'''—OH present. The transition metal preferred is palladium in the form of its salt, like for example palladium (II)-acetat or palladium(0)-compounds, an example of which is tetrakis(triphenylphosphine)palladium. Examples for such kind of CO-insertions can be found in *J. Org. Chem.* 1992, 57, 5979.

Compounds of general formula III can be prepared by methods known in the art by reacting a carbonyl compound of general formula

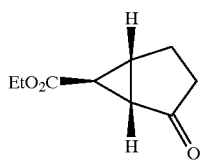

II with a base in the presence of N-phenianesulfonimide) or trifluoromethanesulfonic acid anhydride. The base can be selected from sterically hindered amines, for example 2,6-di-tert.-butyl pyridine or from amides, such as lithium diisopropyl amide. The reaction can be carried out at temperatures between −78° and +20° C. In the case of amine bases, the solvent can be selected from the class of chlorinated solvents, such as, for example, dichloromethane, chloroform or 1,2-dichloroethane. In the case of the amide bases, the solvent can be selected from the class of ethers, for example diethyl ether or tetrahydrofuran.

A general method for the preparation of vinyltrifluoromethanesulfonates can be found in *J. Org. Chem.* 1992,57, 5979.

According to the present invention, compounds of general formula I in which $R^2$ is hydrogen and $R^1$ and $R^{11}$ have the meaning as described above, can be prepared by reducing the azide group of an azide-containing starting compound to an amino group. For example, the azide group of compounds of general formula VII can be reduced to the amino group to obtain compounds of general formula VIII. Ester groups are hydrolyzed to the carboxylic acids. For example, the compounds of general formula VIII can be hydrolyzed to the carboxylic acids as compound I-A. It is also possible to cleave the esters to obtain the carboxylic acids prior to reducing the azide group. For example, compounds of formula VII-I can be cleaved to obtain compounds of general formula XI (cf scheme 2), and subsequently reduce the azide group to the amino group.

A practical method for the reduction of azides to amines is for example the catalytic hydrogenation in the presence of a transition metal catalyst, like for example nickel, platinum or palladium (see for example *Org. Syntheses*, Coll. Vol. V, 1973, 586). Another suitable method is the Staudinger-type reduction of azides using phosphines, like for example triphenyl phosphine in aqueous solutions of an ether, like for example tetrahydrofuran, as described in *J. Chem. Soc. Chem. Comm.* 1986, 409. Still another method for the reduction of azides to amines is the treatment with metal hydrides, like for example lithium aminoborohydride, as shown in: ACS Symp. Ser. 1996, 641 (Reductions in Organic Synthesis), 153–166), or sodium borohydride in the presence of a transition metal salt, like for example nickel (II)chloride hexahydrate, as shown in *Chem. Ind.* (London) 1987, 764.

The cleavage, i.e., hydrolysis, of the ester groups in accordance with the present invention can be achieved by using methods known to those skilled in the art, for example, by treatment of the starting ester with aqueous acid or base at ambient or elevated temperatures, or by the cleavage of esters sensitive to catalytic hydrogenation (for example, benzyl esters and the like) using hydrogen in the presence of a transition metal catalyst like for example nickel, platinum or palladium.

Scheme 2

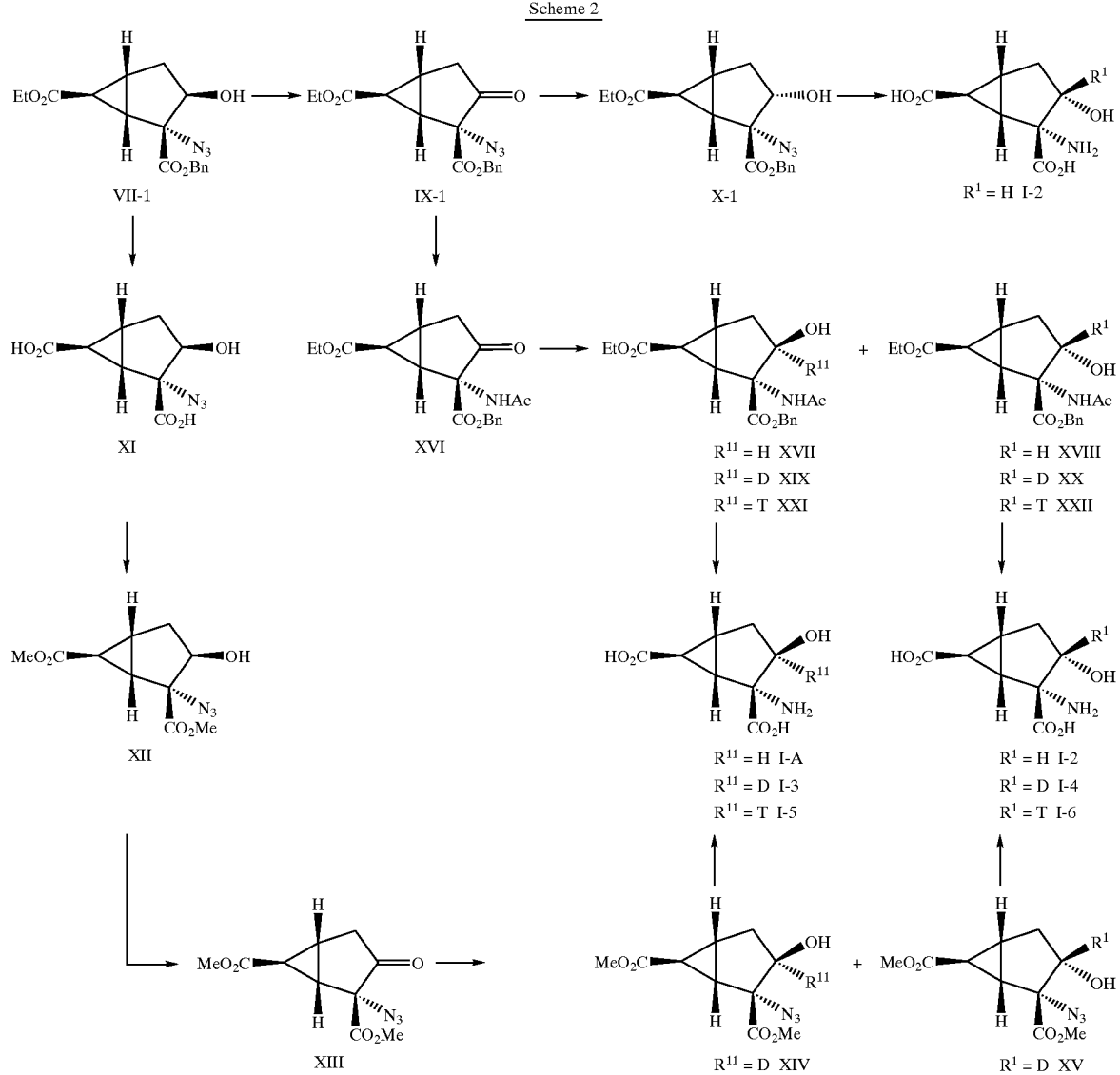

wherein D is deuterium and T is tritium.

According to scheme 2 compounds of general formula I can also be prepared by reducing a compound of the following general formula, wherein moieties R, R', R" and R'" are as shown in scheme 2, as in compounds of formula IX-1, XVI and XIII such that R" and R'" are each independently selected from benzyl or lower alkyl and R and R' are both N$_3$ or R is H and R' is an acyl group,

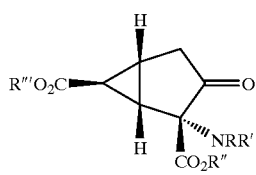

with a reducing agent, for example with sodium-borohydride, lithium- borohydride, sodium-borodeuteride, lithium-borodeuteride, sodium-borotritiide and lithium-trimethoxyborotritiide in the presence or absence of cerium trichloride. The reaction is carried out in solvent mixtures of a protic solvent, for example an alcohol, such as methanol or ethanol, and an ether, such as diethylether or tetrahydrofuran, at temperatures between −78° and +30° C. Although not shown within scheme 2, a compound of formula IX (such as formula IX-1), can be reduced to obtain a compound of formula VII and a compound of formula X (such as formula X-1 as shown). Variation of the conditions of the reduction reaction such as solvent composition, the temperature, the reducing agent used, the presence or absence of cerium trichloride, as well as the transformation of the azide into an N-acylamino group by a reaction prior to reduction of the ketone, like for example the shown reaction of IX to XVI by treatment with thioacetic acid as described in *J. Org. Chem.* 1988, 53, 1581, allows one skilled in the art to obtain the desired diastereoisomer of compounds of general formula I, in which $R^1$ represents hydroxy, $R^{11}$ represents hydrogen, deuterium or tritium and $R^2$ represents hydrogen.

A comprehensive overview for the use of reducing agents can be found in Larock, *Comprehensive Organic Transformations*, Verlag Chemie 1989, 527.

Compounds of general formula IX can be prepared by oxidizing a compound of general formula VII. The reaction is carried out in a chlorinated solvent, for example in dichloromethane, chloroform or dichloroethane. Suitable oxidizing agents are, for example derivatives of chromic acid, such as PDC or PCC, or hypervalent iodine-compounds, such as IBX or the Dess-Martin-reagent. The reaction is preferably carried out at temperatures between −20° and +30° C. under an inert atmosphere.

A comprehensive overview for oxidations using the reagents described above can be found in R. C. Larock, *Comprehensive Organic Transformations*, Verlag Chemie 1989, 604.

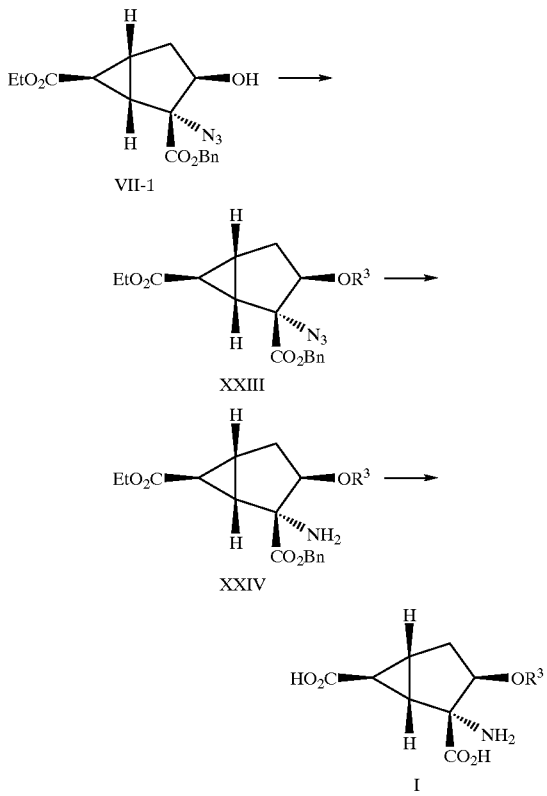

Scheme 3

According to scheme 3 the O-alkylated compounds of general formula I, wherein $R^3$ is lower alkyl (I-7 and I-8), lower alkenyl (I-9) or benzyl (I-10) can be prepared from compounds of the general formulae XXIII (XXIII-1 with $R^3$=CH$_3$; XXIII-2 with $R^3$=allyl; and XXIII-3 with $R^3$=benzyl;)and XXIV (XXIV-1 with $R^3$=CH$_3$; XXIV-2 with $R^3$=allyl; and XXIV-3 with $R^3$=benzyl;)by the methods described above for the preparation of compound I-A.

Compounds of general formula XXIII in which $R^3$ represents lower alkyl, lower alkenyl or benzyl can be prepared by reacting a compound of general formula VII-1 with a trichloroacetimidate of general formula

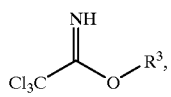

in which $R^3$ represents lower alkyl, lower alkenyl or benzyl in an aprotic solvent in the presence of an acid. In this manner a compound of formula VII can be alkylated, alkenylated or benzylated.

The acid, which is preferably used in catalytic amounts, can be a Bronsted-acid such as trifluoromethane sulfonic acid or trifluoroacetic acid or a Lewis-acid such as trimethylsilyl-trifluoromethane sulfonate or borontrifluoride-etherate. Suitable solvents are preferably aprotic solvents like ethers, such as diethylether or tetrahydrofuran, chlorinated solvents, such as for example dichloromethane, chloroform or dichloroethane, or mixtures of chlorinated solvents and hydrocarbons, such as hexane or cyclohexane. The reaction can be carried out at temperatures between −50° and +40° C. under an inert atmosphere.

Another way to prepare the compounds of general formula I in which $R^1$ represents lower alkyl, lower alkenyl or benzyl is the treatment of compounds of general formula VII with a trifluoromethanesulfonate of general formula

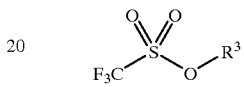

in which $R^3$ has the meaning as described above, in a suitable solvent and in the presence of a base. This is another way in which a compound of formula VII can be alkylated, alkenylated or benzylated.

The base can be selected from the group of sterically hindered amines like, for example, but not limited to, 2,6-di-tert.-butyl-pyridine. The reaction is preferably carried out in aprotic solvents, for example ethers, such as diethyl-ether or tetrahydrofuran, chlorinated solvents, for example dichloromethane, chloroform or dichloroethane or mixtures of chlorinated solvents or hydrocarbons, for example hexane or cyclohexane. The reaction is preferably carried out at temperatures between −50° and +50° C. under an inert atmosphere.

Still another way to alkylate, alkenylate or benzylate a compound of formula VII and thus prepare compounds of general formula XXIII in which $R^3$ represents lower alkyl, lower alkenyl or benzyl, is the treatment of compounds of general formula VII with electrophilic agents of general formula $$R^3-X$$

in which $R^3$ has the meaning as described above and X represents a leaving group, for example iodide, bromide, methanesulfonate and tolylsulfonate, in a suitable solvent in the presence of a base. The reaction is preferably carried out in polar, aprotic solvents, for example chlorinated solvents such as dichloromethane, chloroform or dichloroethane, or amides, for example, dimethylformamide and N-methyl-pyrrolidinone. The base can be selected from the group of sterically hindered amines, for example, but not limited to, 2,6-di-tert.-butyl-pyridine or from the hydride-type such as, for example, sodium hydride or potassium hydride. Other possible bases can be selected from the group of amides, such as for example, sodium hexamethyl disilazide or lithium diisopropylamide. The reaction is preferably carried out at temperatures between −50° and +50° C. under an inert atmosphere.

Scheme 4

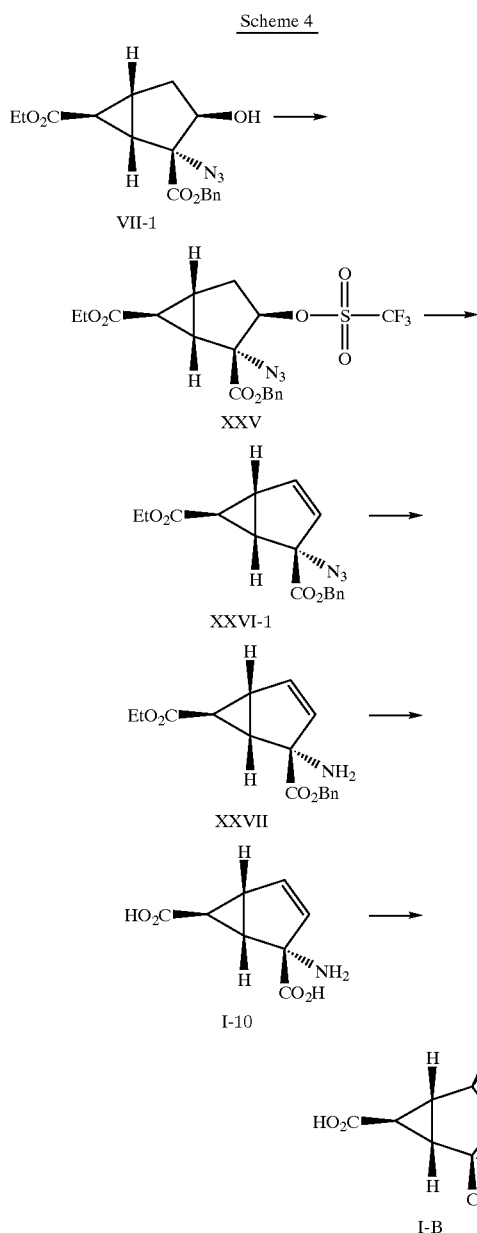

According to scheme 4 compounds of general formula I, in which $R^1$ represents hydrogen and $R^{11}$ and $R^2$ represent tritium can be prepared by treating a compound of general formula

XXVI-1

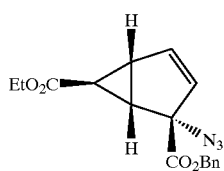

with a mixture of hydrogen and tritiunrence of a transition metal. If desired, the ester groups may be transformed to the carboxylates prior to the concomitant reduction of the azide group.

Compounds of general structure

I-10

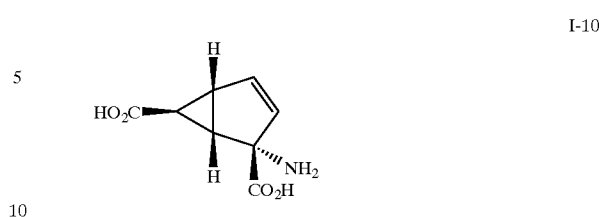

can be prepared by reducing the azide group in compounds of general formula XXVI using the reagents and conditions as described above, preferably with trimethylphosphine as the reducing agent. The reduction is preferably carried out under the conditions as described above for the use of triphenylphosphine. Then the ester groups can be transformed into carboxylic acids by the methods as described above. Again, if desired, the ester groups may be transformed to the carboxylates prior to the reduction of the azide group.

Compounds of general formula XXVII can be prepared by eliminating the anion of trifluoromethane sulfonic acid from a compound of general formula

XXV

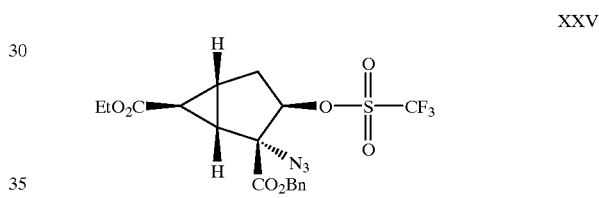

in the presence of a base.

The reaction can be carried out in aprotic solvents, for example ethers, such as diethyl ether or tetrahydrofuran at temperatures between 20° and 35° C. (diethylether), respectively 20° and 50° C. (tetrahydrofuran). The base may be selected from the amine bases, like for example DBU and the like.

Compounds of general formula XXV may be prepared by converting compounds of general formula VII into their trifluoromethanesulfonyl esters. Formula VII can be reacted with trifluoromethane sulfonic acid anhydridesuch that the hydroxy group is transformed into a leaving group, as in the case of formula XXV, trifluoro-methyl sulfonic ester group. The reaction is a standard reaction in organic chemistry and can be carried out as described in Larock, *Comprehensive Organic Transformations,* Verlag Chemie 1989, 360.

Scheme 5

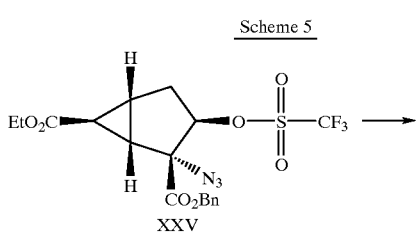

-continued

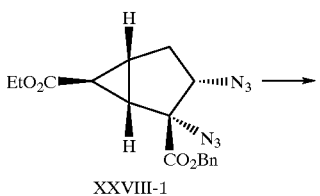
XXVIII-1

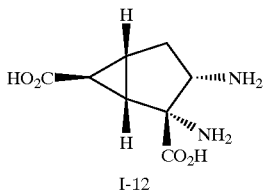
I-12

According to scheme 5 compounds of general formula I, in which R¹ and R² represent hydrogen and R¹¹ represents amino can be prepared from compounds of general formula

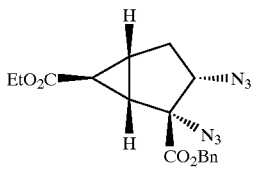
XXVIII-1 by reduction of the azide groups using the reagents and conditions as described above. Then the ester groups can be transformed into carboxylic acids by the methods as described above. If desired, the ester groups may be transformed to the carboxylates prior to the reduction of the azide groups.

Compounds of general formula XXVIII can be prepared by substituting the trifluoromethyl sulfonyl group in compounds of general formula

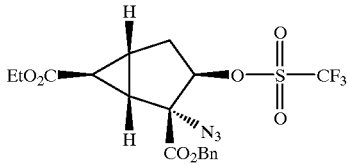
XXV with an azide-containing reagent, preferably sodium azide, in a polar, aprotic solvent like for example DMF at temperatures of around 60° to 100° C.

Compounds of formula I-A may be used in the control or prevention of acute and chronic neurological conditions and psychiatric disorders. In "Mol. Pharmacology, Vol.53, 228–233, (1998)" it is described the in vitro binding of a selective group II metabotropic glutamate receptor radioligand, [3H]LY354740 in rat brain. The inhibition by LY354740 was antagonised with the group II selective competitive antagonist of the compound of formula I-A (pKB=6.0; Ki mGluR2=0.052 μM; Ki mGluR3=0.089 μM).

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant material can be added and include preservatives, stabilizers, wetting or emulsifying agents, salts to change the osmotic pressure or to act as buffers. The pharmaceutical preparations can also contain other therapeutically active substances.

The dosage can vary within wide limits and will, of course, be fitted to the individual requirements in each particular case. In the case of oral administration the dosage lies in the range of about from 1 mg per day dosage to about 1000 mg per day of a compound of general formula I for a patient weighing about 70 kg, although the upper limit can also be exceeded when this is shown to be indicated. In particular, the compound of formula I-A can be used to control or prevent acute or chronic neurological conditions or psychiatric disorders by administering to a patient in need of treatment an amount of from about 1 mg to about 1000 mg per day of the compound of formula I-A.

The following Examples illustrate the present invention without limiting it. All temperatures are given in degrees Celsius.

EXAMPLE 1

(1RS,5SR,6RS)-2-Trifluoromethanesulfonyloxy-bicyclo[3.1.0]hex-2-ene-carboxylic acid ethyl ester (III)

To a solution of diisopropylamine (11.94 mL, 84.6 mmol) in THF (77 mL) was added dropwise n-BuLi (47.6 mL, 76.1 mmol, 1.6 M solution in hexane) at 0° C. and stirred for 10 min at 0° C. After cooling to −78° C. a solution of (1S,5R, 6S)-2-oxo-bicyclo[3.1.0]hexane-6-carboxylic acid ethyl ester (II) (11.86 g, 70.5 mmol) in THF (39 mL) was added dropwise within 25 min. Stirring was continued at −78° C. for 1 h, whereupon a solution of N-phenyl-bis (trifluoromethylsulfonyl)imine (27.7 g, 77.5 mmol) in THF (83 mL) was added and then stirred for 90 min at 23° C. Aqueous workup with ether, sat. NaHCO₃-sol., brine, drying over Na₂SO₄, removal of the solvent under vacuum left an orange-brown oil, which was purified by silica gel column chromatography with hexane/ethyl acetate 9:1 to give (1RS, 5SR,6RS)-2-trifluoromethanesulfonyloxy-bicyclo[3.1.0] hex-2-ene-carboxylic acid ethyl ester (III) (18.47 g, 87%) as a slightly brown oil. ¹H-NMR (250 MHz, CDCl₃) □1.27 (3H, t, J=7.1 Hz), 1.46 (1H, m), 2.28 (1H, m), 2.55 (2H, m),2.79 (1H, m), 4.15 (2H, q, J=7.1 Hz), 5.4 (1H, m); MS[EI] 300 (M⁺).

EXAMPLE 2

(1RS,5SR,6RS)-Bicyclo[3.1.0]hex-2-ene-2,6-dicarboxylic acid 2-benzyl ester 6-ethyl ester (IV)

A solution of (1RS,5SR,6RS)-2-trifluoromethanesulfonyloxy-bicyclo[3.1.0]hex-2-ene-carboxylic acid ethyl ester (III) (14.48 g, 48.2 mmol), Pd(OAc)₂ (326 mg, 1.45 mmol), PPh₃ (760 mg, 2.9 mmol), benzyl alcohol (10.0 mL, 96.5 mmol) and Et₃N (13.5 mL, 96.5 mmol) in DMF (195 mL) was purged with CO for 10 min and then stirred for 5 h at 23° C. under a balloon with CO. Aqueous workup with ether, 1 N HCl-sol., sat. NaHCO₃-sol. and brine was followed by drying over MgSO₄. Removal of the solvent under vacuum left a dark brown oil, which was purified by silica gel column chromatography with hexane/ethyl acetate 9:1 to yield (1RS, 5SR,6RS)-bicyclo[3.1.0]hex-2-ene-2,6-dicarboxylic acid 2-benzyl ester 6-ethyl ester (IV) (10.36 g, 75%) as a yellow oil. $^1$H-NMR (250 MHz, CDCl$_3$) ☐1.13 (1H, m), 1.26 (3H, t, J=7.1 Hz), 2.25 (1H, m), 2.64 (1H, m), 2.79–2.91 (2H, m), 4.10 (2H, q, J=7.1 Hz), 5.18 (1H, d, J=12 Hz), 5.24 (1H, d,J=12 Hz), 6.58 (1H, bs), 7.30–7.40 (5H, m); MS[EI]286 (M$^+$).

EXAMPLE 3

(1S,2S,3R,6S)-2,3-Dihydroxy-bicyclo[3.1.0]hexane-2,6-dicarboxylic acid 2-benzyl ester 6-ethyl ester (V)

A solution of (1RS,5SR,6RS)-bicyclo[3.1.0]hex-2-ene-2,6-dicarboxylic acid 2-benzyl ester 6-ethyl ester (IV) (11.69 g, 40.4 mmol), K$_2$[OsO$_2$(OH)$_4$](99 mg, 0.27 mmol), (DHQD)$_2$PHAL (1.05 g, 1.35 mmol), K$_3$Fe(CN)$_6$ (26.6 g, 80.8 mmol), K$_2$CO$_3$ (11.2 g, 80.8 mmol) and MeSO$_2$NH$_2$ (11.53 g, 121.2 mmol) in tert.-butanol (140 mL) and H$_2$O (140 mL) was stirred vigorously at 4° C. for 24 h. After addition of Na$_2$SO$_3$ (40.4 g) and stirring for 30 min at 23° C. the mixture was diluted with water (300 mL) and extracted with ethyl acetate (3×300 mL). The combined organic layers were washed with 2 N NaOH-sol. (200 mL) and brine (200 mL) followed by drying over Na$_2$SO$_4$. Removal of the solvent under vacuum left a dark brown solid (13.51 g), which was subjected to silica gel column chromatography with hexane/ethyl acetate 2:1->3:2->1:1 to yield the residual starting material as a yellow oil (3.58 g, 31%, 65% ee), the undesired diastereomeric diol as a yellow oil (1.30 g. 10%) and the crystalline diol (1S,2S,3R,6S)-2,3-dihydroxy-bicyclo [3.1.0]hexane-2,6-dicarboxylic acid 2-benzyl ester 6-ethyl ester (5.91 g, 45.7%, 63% ee) as a pale yellow solid. The latter material was twice recrystallized from ethyl acetate/ether/hexane to give enantiopure (1S,2S,3R,6S)-2,3-dihydroxybicyclo[3.1.0]hexane-2,6-dicarboxylic acid 2-benzyl ester 6-ethyl ester (V) (3.36 g, 26%, >99% ee) as white needles. $^1$H-NMR (250 MHz, CDCl$_3$) ☐1.24 (3H, t, J=7.1 Hz), 1.80–1.92 (2H, m), 1.99 (1H, m), 2.08 (1H, dd, J=6.9,2.9 Hz), 2.30–2.38 (2H, m), 3.82 (1H, s), 4.10 (2H, q, J=7.1 Hz), 5.20 (1H, d, J=12.3 Hz), 5.34 (1H, d, J=12.3 Hz), 7.36 (5H, bs); MS[ISP]321 (M+H$^+$); mp 112–114° C. ☐$_D^{20}$–73.35°(c=1.17, CHCl$_3$).

EXAMPLE 4

(1S, 1aS,1bS,4aR,5aR)-3,3-Dioxo-tetrahydro-2,4-dioxa-6-thia-cylopropa[a]pentalene-1,1b-dicarboxylic acid 1b-benzul ester 1-ethyl ester (VI)

To a solution of (1S,2S,3R,6S)-2,3-dihydroxy-bicyclo [3.1.0]hexane-2,6-dicarboxylic acid 2-benzyl ester 6-ethyl ester (V) (2.66 g, 8.32 mmol) in CH$_2$Cl$_2$ (14 mL) at 0° C. was added SOCl$_2$ (1.21 mL, 16.64 mmol) and stirring was continued at 40° C., until tlc indicated complete conversion to the cyclic sulfite. The solvent and excess SOCl$_2$ were removed under vacuum, the residual oil was dissolved in CCl$_4$ (8.3 mL), CH$_3$CN (8.3 mL) and H$_2$O (12.5 mL) and cooled to 0° C. NaIO$_4$ (2.67 g, 12.5 mmol) and RuCl$_3$ hydrate (33 mg) were added and the mixture was stirred at 23° C. for 30 min. Aqueous workup with ether, water and brine was followed stirring of the organic phase with MgSO$_4$ and a spatula tip of activated carbon. After filtration throught celite the solvent was removed under vacuum to yield a pale the crude cyclic sulfate as a brown oil (3.31 g). An analytical sample was obtained by silica gel column chromatography with hexane/ethyl acetate 2:1 to yield (1S,1aS,1bS,4aR,5aR)-3,3-dioxo-tetrahydro-2,4-dioxa-6-thiacyclopropa[a]pentalene-1,1b-dicarboxylic acid 1b-benzyl ester 1-ethyl ester (VI) (98%). $^1$H-NMR (250 MHz, CDCl$_3$) ☐1.25 (3H, t,J=7.2 Hz), 1.67 (1H, t, J=3.5 Hz), 2.28 (1H, m), 2.52–2.62 (3H, m), 4.11 (2H, m), 5.32 (2H, s), 7.38 (5H, s); MS[ISP] 400 (M+NH$_4^+$); ☐$_D^{23}$36.08°(c=1.13, CHCl$_3$).

EXAMPLE 5

(1S,2R,3R,5R,6S)-2-Azido-3-hydroxy-bicyclo[3.1.0]hexane-2,6-dicarboxylic acid 2-benzyl ester 6-ethyl ester (VII-1)

The crude cyclic sulfate VI was dissolved in acetone (45 mL) and H$_2$O (4.5 mL), NaN$_3$ (720 mg, 11.1 mmol) was added and the mixture was stirred at 50° C. until tlc indicated complete conversion of the cyclic sulfate. The solvent was removed under vacuum, the residue partitioned between ether (160 mL) and water (4.5 mL), cooled to 0° C., whereupon 20% H$_2$SO$_4$ (13.5 mL) was dropwise added. The mixture was stirred vigorously at 23° C. for 37 h, the layers were separated, the organic layer washed with sat. NaHCO$_3$-sol. and brine, dried over MgSO$_4$. After removal of the solvent under vacuum, the residual oil (2.78 g, 97%) was purified by silica gel column chromatography with hexane/ ethyl acetate 9:1–>5:1 to give (1S,2R,3R,5R,6S)-2-azido-3-hydroxy-bicyclo[3.1.0]hexane-2,6-dicarboxylic acid 2-benzyl ester 6-ethyl ester (VII-1) (1.79 g, 62%) as a colorless oil. $^1$H-NMR (250 MHz, CDCl$_3$) ☐1.26 (3H, t, J=7.1 Hz), 1.81 (1H, t, J=3.1 Hz), 2.04–2.20 (3H, m), 2.25 (1H, dd, J=6.9, 2.9 Hz), 2.34 (1H, dd, J=7.7, 3.9 Hz), 3.80 (1H, bq, J=9 Hz), 4.12 (2H, q, J=7.1 Hz), 5.27 (1H, d, J=12.2 Hz), 5.34 (1H, d, J=12.2 Hz), 7.36–7.40 (5H, m); MS[ISN] 404 (M+OAc$^-$); ☐$_D^{20}$–48.43° (c=1.09, CHCl$_3$).

EXAMPLE 6

(1S,2R,3R,5R,6S) -2-Amino-3-hydroxy-bicyclo[3.1.0]hexane-2,6-dicarboxylic acid (I-A)

A solution of (1S,2R,3R,5R,6S)-2-azido-3-hydroxy-bicyclo [3.1.0]hexane-2,6-dicarboxylic acid 2-benzyl ester 6-ethyl ester (VII-1) (1.55 g, 4.49 mmol) in HOAc (20 mL) and H$_2$O (5 mL) was hydrogenated in the presence of Pd/C (100 mg, 10% Pd/C) at 23° C. for 18 h. The catalyst was removed by filtration, the filter cake washed with 50% aqueous acetic acid. After removal of the solvent in vacuum, the beige residue was refluxed in 10% HCl (55 mL) for 4 h. The solution was cooled to 23° C., filtered, washed with water and evaporated to dryness. The remaining pale yellow solid was dissolved in EtOH (45 mL) and propylene oxide (24 mL) and refluxed for 15 min, whereupon the amino acid precipiated. After cooling to 23° C., the product was filtered off, washed with ether and dried to give (1S,2R,3R,5R,6S)-2-amino-3-hydroxy-bicyclo [3.1.0]hexane-2,6-dicarboxylic acid (I-A) (784 mg, 87%) as a white solid. $^1$H-NMR (250 MHz, D$_2$O) ☐1.87 (1H, t, J=3.1 Hz), 2.15–2.26 (3H, m), 2.38 (1H, dd, J=13.0, 7.6 Hz), 3.97 (1H, dd,J=8.6,7.4 Hz); MS[ISP]202 (M+H$^+$); mp>250° C.; ☐$_D^{20}$+7.41° (c=1.01, H$_2$O).

EXAMPLE 7

(1S,2R,3R,5R,6S)-2-Amino-3-hydroxy-bicyclo[3.1.0]hexane-2,6-dicarboxylic acid 2-benzyl ester 6-ethyl ester (VIII)

To a solution of (1S,2R,3R,5R,6S)-2-azido-3-hydroxy-bicyclo[3.1.0]hexane-2,6-dicarboxylic acid 2-benzyl ester 6-ethyl ester (VII-1) (200 mg, 0.58 mmol) in MeOH (5.8 mL) and a few drops of chloroform at 0° C. was added NiCl$_2$.6 H$_2$O (661 mg, 2.78 mmol) was dissolved in acetone (45 mL) and H$_2$O (4.5 mL), NaN$_3$ (720 mg, 11.1 mmol) and stirred for 10 min at 0° C. Upon cautious addition of NaBH$_4$ (175 mg, 4.62 mmol) the reaction mixture turned immediately black, stirring was continued at 0° C. for 10 min and then hydrolyzed with water and ether. After additional stirring for 10 min at 0° C., the reaction mixture was extracted with ether, washed with brine (2×50 mL) and dried over Na$_2$SO$_4$ and filtered through celite. The solvent was removed under vacuum, the residue was purified by silica gel column chromatography with ethyl acetate/MeOH 95:5 (+0.6% Et$_3$N) to give (1S,2R,3R,5R,6S)-2-amino-3-hydroxy-bicyclo[3.1.0]hexane-2,6-dicarboxylic acid 2-benzyl ester 6-ethyl ester (VIII) (106 mg, 57%) as a yellow oil. $^1$H-NMR (250 MHz, CDCl$_3$) ☐1.25 (3H, t, J=7.1 Hz), 1.75 (1H, t,J=3.5 Hz), 1.97 (1H, m), 2.12 (1H, dd,J=7, 3.5 Hz), 2.14–2.28 (4H, m), 2.33 (1H, dd,J=12.5, 7 Hz), 3.65 (1H, dd, J=8, 7 Hz), 4.10 (2H, q, J=7.1 Hz), 5.22 (1H, d, J=12.5 Hz), 5.27 (1H, d, J=12.5 Hz), 7.38 (5H, m); MS[ISP] 320 (M+H$^+$); ☐$_D^{20}$–0.56° (c=0.89, CHCl$_3$).

EXAMPLE 8

(1S,2R,5R,6S)-2-Azido-3-oxo-bicyclo[3.1.0]hexane-2,6-dicarboxulic acid 2-benzyl ester 6-ethyl ester (IX-1)

To a solution of ( 1S,2R,3R,5R,6S)-2-Azido-3-hydroxy-bicyclo [3.1.0] hexane-2,6-dicarboxylic acid 2-benzyl ester 6-ethyl ester (VII-1) (960 mg, 2.78 mmol) in DCM (18 mL) was added PCC (2.40 g, 50% on silica gel) at 0° C. and stirring was continued at 23° C. for 20 h. The reaction mixture was placed on a silica gel column and the product was eluted with DCM to yield (1S,2R,5R,6S)-2-azido-3-oxo- bicyclo[3.1.0]hexane-2,6-dicarboxylic acid 2-benzyl ester 6-ethyl ester (IX-1) (746 mg, 78%) as a white solid. $^1$H-NMR (250 MHz, CDCl$_3$) ☐1.27 (3H, t, J=7.2 Hz), 1.62 (1H, t,J=3.4 Hz), 2.29 (1H, m), 2.44 (1H, dd,J=7.7, 3.1 Hz), 2.55 (1H, d, J=19.2 Hz), 2.98 (1H, dd, J=19.2, 5.6 Hz), 4.13 (2H, q, J=7.2 Hz), 5.29 (2H, s), 7.36–7.40 (5H, m); MS[ISP] 361 (M+NH$_4^+$); mp 46–48° C.; ☐$_D^{20}$+210.910 (c=1.07, CHCl$_3$).

EXAMPLE 9

(1S,2R,3S,5R,6S)-2-Azido-3-hydroxy-bicyclo[3.1.0]hexane-2,6-dicarboxylic acid 2-benzyl ester 6-ethyl ester (X-1)

To a solution of (1S,2R,5R,6S)-2-azido-3-oxo-bicyclo[3.1.0]hexane-2,6-dicarboxylic acid 2-benzyl ester 6-ethyl ester (IX-1) (100 mg, 0.29 mmol) in EtOH (1.7 mL) and THF (0.5 mL) was added NaBH$_4$ (22 mg, 0.58 mmol) at –50° C. and stirring was continued at –50° C. for 4 h. The reaction mixture was poured on ice, acidified with 1 N HCl and extracted with ether. After washing with sat. NaHCO$_3$-sol., brine and drying over MgSO$_4$ the crude product was purified by silica gel column chromatography with hexane/EtOAc 5:1 to give (1 S,2R,3S,5R,6S)-2-azido-3-hydroxy-bicyclo[3.1.0]hexane-2,6-dicarboxylic acid 2-benzyl ester 6-ethyl ester (X-1) (51 mg, 51%) as a colorless oil. $^1$H-NMR (250 MHz, CDCl$_3$) ☐1.26 (3H, t, J=7.2 Hz), 2.03–2.18 (3H, m),2.31–2.48 (2H, m),2.53 (1H, t,J=4 Hz),4.13 (2H, q,J=7.2 Hz), 4.21 (1H,bs), 5.26 (2H, s), 7.36–7.40 (5H, m); MS [EI]300 [(M—OEt)$^+$];

EXAMPLE 10

(1S,2R,3S,5R,6S)-2-Amino-3-hydroxy-bicyclo[3.1.0]hexane-2,6-dicarboxylic acid (I-2)

A solution of ( 1S,2R,3S,5R,6S)-2-azido-3-hydroxy-bicyclo [3.1.0] hexane-2,6-dicarboxylic acid 2-benzyl ester 6-ethyl ester (X-1) (50 mg, 0.145 mmol) in HOAc (4 mL) and H$_2$O (1 mL) was hydrogenated in the presence of Pd/C (11 mg, 10% Pd/C) at 23° C. for 23 h. The catalyst was removed by filtration, the filter cake washed with 50% aqueous acetic acid. After removal of the solvent in vacuum, the beige residue was refluxed in 10% HCl (6.75 mL) for 4 h. The solution was cooled to 23° C., filtered, washed with water and evaporated to dryness. The remaining pale yellow solid was dissolved in EtOH (5 mL) and propylene oxide (2 mL) and refluxed for 15 min, whereupon the amino acid precipiated. After cooling to 23° C., the product was filtered off, washed with ether and dried to give (1S,2R,3S,5R,6S)-2-amino-3-hydroxy-bicyclo[3.1.0]hexane-2,6-dicarboxylic acid (I-2) (24 mg, 86%) as a white solid. $^1$H-NMR (250 MHz, D$_2$O) ☐2.05 (1H, d,J=15 Hz), 2.10–2.20 (2H, m), 2.12 (1H, m), 2.61 (1H, m), 4.20 (1H, d, J=7.2 Hz); MS[ISP] 202 (M+H$^+$); mp 208° C. (dec.); ☐$_D^{20}$+27.52° (c=1.03, H$_2$O).

EXAMPLE 11

(1S,2R,3R,5R,6S)-2-Azido-3-hydroxy-bicyclo[3.1.0]hexane-2,6-dicarboxylic acid (XI)

To a solution of (1S,2R,3R,5R,6S)-2-azido-3-hydroxy-bicyclo[3.1.0]hexane-2,6-dicarboxylic acid 2-benzyl ester 6-ethyl ester (VII) (845 mg, 2.45 mmol) in THF (21 mL) and H$_2$O (6 mL) was added LiOH.H$_2$O (411 mg, 9.8 mmol) and the mixture was stirred at 23° C. for 18 h. The benzyl alcohol was extracted with ether, the aqueous layer acidified with 1 M KHSO$_4$-sol., saturated with solid NaCl, extracted with EtOAc (4×50 mL) and dried over MgSO$_4$. After removal of the solvent under vacuum crude (1S,2R,3R,5R,6S)-2-azido-3-hydroxy-bicyclo[3.1.0]hexane-2,6-dicarboxylic acid (XI) (581 mg, quant.) was obtained as white solid, sufficiently pure for further transformations. $^1$H-NMR (250 MHz, DMSO) ☐1.75 (1H, t, J=3.5 Hz), 1.84 (1H, m), 1.92–2.07 (2H, m), 2.15 (1H, dd, J=12.5, 7 Hz), 3.87 (1H, btJ=7 Hz); MS[ISN] 226 [(M-H)–]; mp 124–128° C.; ☐$_D^{20}$–61.48° (c=0.90, H$_2$O).

EXAMPLE 12

(1S,2R,3R,5R,6S)-2-Azido-3-hvdroxy-bicyclo[3.10] hexane-2,6-dicarboxylic acid dimethyl ester (XII)

Crude (1S,2R,3R,5R,6S)-2-azido-3-hydroxy-bicyclo [3.1.0] hexane-2,6-dicarboxylic acid (XI) (515 mg, 2.27 mmol) was dissolved in MeOH (20 mL) and stirred in the presence of conc. H$_2$SO$_4$ (0.1 mL) at 23° C. for 7 d. The mixture was diluted with ether, washed with sat. NaHCO$_3$-sol., brine and dried over MgSO$_4$. After removal of the solvent in vacuum, the residue was purified by silica gel column chromatography with hexane/ethyl acetate 2:1 to give (1S,2R,3R,5R,6S)-2-azido-3-hydroxy-bicyclo[3.1.0]hexane-2,6-dicarboxylic acid dimethyl ester (XII) (500 mg, 86%) as a yellow oil. $^1$H-NMR (250 MHz, CDCl$_3$) ☐1.84 (1H, t, J=3.1 Hz), 2.04–2.26 (2H, m),2.25 (1H, dd,J=6.9, 3.0 Hz), 2.37 (1H, dd,J=12.5, 7.8 Hz), 3.69 (3H, s), 3.83 (1H, bq, J=9 Hz), 3.90 (3H, s); MS [ISP] 273 (M+NH$_4^+$); ☐$_D^{20}$–53.33° (c=1.11, CHCl$_3$).

EXAMPLE 13

(1S,2R,5R,6S)-2-Azido-3-oxo-bicyclo[3.1.0]hexane-2,6-dicarboxylic dimethyl ester (XIII)

To a solution of (1S,2R,3R,5R,6S)-2-azido-3-hydroxy-bicyclo[3.1.0]hexane-2,6-dicarboxylic acid dimethyl ester (XII) (239 mg, 0.94 mmol) in DCM (6 mL) was added PCC (1.13 g, 2.62 mmol, 50% on silica gel) at 0° C. and the mixture was stirred at 23° C. for 2 d. The PCC was removed by filtration through a silica gel column and the pure (1S,2R,5R,6S)-2-azido-3-oxo-bicyclo[3.1.0]hexane-2,6-dicarboxylic dimethyl ester (XIII) was obtained by silica gel column chromatography with hexane/EtOAc 2:1 as a white solid (152 mg, 64%). $^1$H-NMR (250 MHz, CDCl$_3$) δ1.64 (1H, t,J=3.4 Hz), 2.34 (1H, ddd,J=7.7, 5.5, 3.2 Hz), 2.46 (1H, dd,J=7.7, 3.1 Hz), 2.56 (1H, d,J=19.2 Hz), 3.06 (1H, dd, J=19.2, 5.5 Hz), 3.71 (3H, s), 3.89 (3H, s); MS[EI] 222 [(M-OCH$_3$)$^+$]; mp 62–65° C.;

EXAMPLE 14

(1S,2R,3R,5R.6S)-2-Azido-3-deutero-3-hydroxy-bicyclo [3.1.0] hexane-2,6-dicarboxylic acid dimethyl ester (XIV) and (1S,2R,3S,5R,6S)-2-Azido-3-deutero-3-hydroxy-bicyclo[3.1.0]hexane-2,6-dicarboxylic acid dimethyl ester (XV)

A suspension of (1S,2R,5R,6S)-2-azido-3-oxo-bicyclo [3.1.0]hexane-2,6-dicarboxylic dimethyl ester (XIII) (123 mg, 0.486 mmol) and anhydrous CeCl$_3$ (120 mg, 0.486 mmol) in MeOH (3.8 mL) was sonicated at 23° C. for 2 min and cooled to −78° C. NaBD$_4$ (21 mg, 0.486 mmol) was added in one portion and the mixture was stirred at −50° C. for 30 min. The reaction was quenched by addition of HOAc (ca. 0.5 mL), warming up to 23° C. and stirring for 10 min. After dilution with ether and extraction with sat. NaHCO$_3$-sol., brine and drying over MgSO$_4$ the crude product was purified by silica gel column chromatography with hexane/ EtOAc 2:1 to give (1S,2R,3S,5R,6S)-2-azido-3-deutero-3-hydroxy-bicyclo [3.1.0]hexane-2,6-dicarboxylic acid dimethyl ester (XV) (47 mg, 38%, less polar product) and (1S,2R,3R,5R,6S)-2-azido-3-deutero-3-hydroxy-bicyclo [3.1.0]hexane-2,6-dicarboxylic acid dimethyl ester (XIV) (15 mg, 12%, more polar product) both as a colorless oil. (XV): $^1$H-NMR (250 MHz, CDCl$_3$) δ2.04–2.11 (2H, m), 2.20 (1H, bs), 2.36 (1H, dd, J=6.6, 3.0 Hz), 2.45 (1H, dd, J=13, 5.5 Hz), 2.56 (1H, t, J=3.1 Hz), 3.70 (3H, s), 3.85 (3H, s); MS[ISP] 274 (M+NH$_4^+$); (XIV): $^1$H-NMR (250 MHz, CDCl$_3$) δ1.84 (1H, t, J=3.5 Hz), 2.07 (1H, dd, J=6.5, 3.5 Hz), 2.16 (1H, dd, J=12.5, 5.5 Hz), 2.27 (1H, dd,J=6.5,3.5 Hz), 2.33 (1H, s), 2.37 (1H, d,J=12.5Hz),3.69 (3H, s), 3.90 (3H, s); MS[ISP] 274 (M+NH$_4^+$);

EXAMPLE 15

(1S,2R,3R,5R,6S)-2-Amino-3-deutero-3-hydroxy-bicyclo [3.10]hexane-2,6-dicarboxylic acid (I-3)

A solution of (1S,2R,3R,5R,6S)-2-azido-3-deutero-3-hydroxy-bicyclo [3.1.0]hexane-2,6-dicarboxylic acid dimethyl ester (XIV) (15 mg, 0.058 mmol) in HOAc (1 mL) and H$_2$O (0.25 mL) was hydrogenated in the presence of Pd/C (5 mg, 10% Pd/C) at 23° C. for 18 h. The catalyst was removed by filtration and the catalyst washed with water. After removal of the solvent in vacuum, the beige residue was refluxed in 10% HCl (2 mL) for 4 h. The solution was cooled to 23° C.. and evaporated to dryness. The remaining pale yellow solid was dissolved in EtOH (2 mL) and propylene oxide (0.5 mL) and refluxed for 15 min, whereupon the amino acid precipiated as white fluffy material. After cooling to 23° C., the product was filtered off, washed with ether, taken up in water and lyophilized to give (1S,2R,3R,5R, 6S)-2-amino-3-deutero-3-hydroxybicyclo[3.1.0]hexane-2, 6-dicarboxylic acid (I-3) (9 mg, 76%) as a white solid. $^1$H-NMR (250 MHz, D$_2$O) δ1.45 (1H, t,J=3.1 Hz), 1.71 (1H, m), 1.79 (1H, dd, J=7, 3.0 Hz), 1.94 (1H, dd,J=12.5, 5 Hz), 2.17 (1H, d, J=12.6 Hz); MS[ISN] 201 [(M—H)$^{31}$ ] mp>250° C.; [α]$_D^{20}$ 0.94° (c=0.32, H$_2$O).

EXAMPLE 16

(1S,2R,3S,5R,6S)-2-Amino-3-deutero-3-hydroxy-bicyclo [3.1.0]hexane-2,6-dicarboxylic acid (I-4)

A solution of (1S,2R,3S,5R,6S)-2-azido-3-deutero-3-hydroxy-bicyclo [3.1.0]hexane-2,6-dicarboxylic acid dimethyl ester (XV) (47 mg, 0.183 mmol) in HOAc (2 mL) and H$_2$O (0.5 mL) was hydrogenated in the presence of Pd/C (9 mg, 10% Pd/C) at 23° C. for 18 h. The catalyst was removed by filtration and the catalyst washed with water. After removal of the solvent in vacuum, the beige residue was refluxed in 10% HCl (3 mL) for 4 h. The solution was cooled to 23° C. and evaporated to dryness. The remaining pale yellow solid was dissolved in EtOH (3 mL) and propylene oxide (1.5 mL) and refluxed for 15 min, whereupon the amino acid precipiated as white fluffy material. After cooling to 23° C., the product was filtered off, washed with ether, taken up in water and lyophilized to give (1S,2R,3S,5R,6S)-2-amino-3-deutero-3-hydroxy-bicyclo[3.1.0]hexane-2,6-dicarboxylic acid (I-4) (32 mg, 86%) as a white solid. $^1$H-NMR (250 MHz, D$_2$O) δ2.05 (1H, d, J=15 Hz), 2.14 (2H, m), 2.23 (1H, dd, J=7,3.5 Hz), 2.60 (1H, dd. J=15, 5 Hz); MS[ISN] 201 [(M-H)$^-$]; mp>250° C.; [α]$_D^{20}$+31.26° (c=0.12, H$_2$O).

EXAMPLE 17

(1S,2R,5R,6S)-2-Acetylamino-3-oxo-bicyclo[3.1.0] hexane-2,6-dicarboxylic acid 2-benzyl ester 6-ethyl ester (XVI)

A solution of (1S,2R,5R,6S)-2-Azido-3-oxo-bicyclo [3.1.0]hexane-2,6-dicarboxylic acid 2-benzyl ester 6-ethyl ester (IX) (974 mg, 2.84 mmol) in thioacetic acid (6.5 mL) was stirred at 70° C. for 2 d. The reaction mixture was concentrated in vacuum and subjected to silica gel column chromatography with hexane/ethyl acetate 3:2–>1:1 to yield (1S,2R,5R,6S)-2-acetylamino-3-oxo-bicyclo [3.1.0]hexane-2,6-dicarboxylic acid 2-benzyl ester 6-ethyl ester (XVI) (726 mg, 71%) as a pink oil. $^1$H-NMR (250 MHz, CDCl$_3$) δ1.25 (3H, t, 1=7.1 Hz), 1.63 (1H, t, J=3.5 Hz), 2.05 (3H, s), 2.32 (1H, ddd,J=7, 6,3.5 Hz), 2.54 (1H, d,J=19 Hz), 2.90 (1H, dd,J=19, 6 Hz), 3.06 (1H, dd, J=7, 3.5 Hz), 4.12 (2H, m), 5.16 (1H, d, J=12 Hz), 5.25 (1H, d, J=12 Hz), 7.24–7.35 (5H, m); MS[ISP] 360 (M+H$^+$); [α]$_D^{20}$+44.33° (c=0.97, CHCl$_3$).

EXAMPLE 18

(1S,2R,3R,5R,6S)-2-Acetylamino-3-hydroxy-bicyclo[3.1.0]hexane-2,6-dicarboxylic acid 2-benzyl ester 6-ethyl ester (XVII) and (1S,2R,3S,5R,6S)-2-Acetylamino-3-hydroxy-bicyclo [3.1.0]hexane-2,6-dicarboxylic 2-benzyl ester 6-ethyl ester (XVIII)

To a solution of (1S,2R,5R,6S)-2-acetylamino-3-oxo-bicyclo [3.1.0] hexane-2,6-dicarboxylic 2-benzyl ester 6-ethyl ester (XVI) (77 mg, 0.214 mmol) in EtOH (2 mL) and THF (1 mL) was added LiBH$_4$ (5 mg, 0.23 mmol) at −50° C. and the mixture was stirred at −50° C. for 45 min. The reaction was quenched by addition of 1 N HCl (ca. 0.5 mL), warming up to 23° C. and stirring for 10 min. After dilution with ethyl acetate and extraction with sat. NaHCO$_3$-sol., brine and drying over MgSO$_4$ the crude product was purified by silica gel column chromatography with toluene/acetone 3:1 to give (1S,2R,3R,5R,6S)-2-acetylamino-3-hydroxy-bicyclo[3.1.0]hexane-2,6-dicarboxylic acid 2-benzyl ester 6-ethyl ester (XVII) (33 mg, 43%, less polar product) as a colorless oil and (1S,2R,3S,5R,6S)-2-acetylamino-3-hydroxy-bicyclo[3.1.0]hexane-2,6-dicarboxylic acid 2-benzyl ester 6-ethyl ester (XVIII) (35 mg, 45%, more polar product) as a white solid. (XVII): $^1$H-NMR (250 MHz, CDCl$_3$) □1.26 (3H, t, J=7.2 Hz), 1.76 (1H, t, J=3.5 Hz), 2.07 (1H, m), 2.10 (3H, s), 2.16 (1H, dd, J=6.1, 3.0 Hz), 2.30–2.41 (3H, m), 3.97–4.13 (3H, m), 5.24 (2H, bs), 6.19 (1H, bs), 7.26–7.38 (5H, m); MS[ISP] 362 (M+H$^+$); □$_D^{20}$−11.24° (c=1.18, CHCl$_3$). (XVIII): $^1$H-NMR (250 MHz, CDCl$_3$) □1.25 (3H, t, J=7.1 Hz), 1.98 (1H, m), 2.05–2.11 (1H, m), 2.06 (3H, s), 2.18 (1H,t,J=3.5 Hz), 2.27–2.41 (2H, m), 2.59 (1H, ddd,J=13, 7, 5 Hz), 4.12 (2H, m), 4.68 (1H, dd, J=7, 5 Hz), 5.17 (2H, s), 6.30 (1H, bs), 7.26–7.40 (5H, m); MS[ISP] 362 (M+H$^+$); mp 145–147° C.; □$_D^{20}$+42.44° (c=1.01, CHCl$_3$).

EXAMPLE 19

(1S,2R,3R,5R,6S)-2-Acetylamino-3-deutero-3-hydroxy-bicyclo [3.1.0]hexane-2,6-dicarboxylic acid 2-benzyl ester 6-ethyl ester (XIX) and (1S,2R,3S,5R,6S)-2-Acetylamino-3-deutero-3-hydroxy-bicyclo[3.1.0]hexane-2,6-dicarboxylic 2-benzyl ester 6-ethyl ester (XX)

To a solution of (1S,2R,5R,6S)-2-acetylamino-3-oxo-bicyclo [3.1.0] hexane-2,6-dicarboxylic 2-benzyl ester 6-ethyl ester (XVI) (105 mg, 0.292 mmol) in EtOH (1.9 mL) and THF (1.0 mL) was added NaBD$_4$ (24.5 mg, 0.584 mmol) at −50° C. and the mixture was stirred at −50° C. for 90 min. The reaction was quenched by addition of HOAc (ca. 0.5 mL), warming up to 23° C. and stirring for 10 min. After dilution with ethyl acetate, 1 N HCl was added, followed by washings with sat. NaHCO$_3$-sol., brine and drying over MgSO$_4$. After removal of the solvent in vacuum the crude product was purified by silica gel column chromatography with toluene/acetone 3:1 to give (1S,2R,3R,5R,6S)-2-acetylamino-3-deutero-3-hydroxy-bicyclo [3.1.0] hexane-2,6-dicarboxylic acid 2-benzyl ester 6-ethyl ester (XIX) (45 mg, 43%, less polar product) as a colorless oil and (1S,2R,3S,5R,6S)-2-acetylamino-3-deutero-3-hydroxy-bicyclo [3.1.0]hexane-2,6-dicarboxylic acid 2-benzyl ester 6-ethyl ester (XX) (50 mg, 47%, more polar product) as a white solid. (XIX): $^1$H-NMR (250 MHz, CDCl$_3$) □1.26 (3H, t, J=7.2 Hz), 1.98 (1H, m), 1.74 (1H, t, J=3.5 Hz), 2.04–2.10 (1H, m), 2.09 (3H, s), 2.17 (1H, dd, J=7, 2.9 Hz), 2.35–2.40 (3H, m), 4.10 (2H, m), 5.24 (2H, s), 6.33 (1H, bs), 7.26–7.37 (5H, m); MS[ISP] 363 (M+H$^+$); (XX): $^1$H-NMR (250 MHz, CDCl$_3$) □1.24 (3H, t, J=7.1 Hz), 1.97 (1H, ddd, J=8,6.5,3 Hz), 2.04 (3H, s), 2.06 (1H, dd, J=13.5, 3.7 Hz), 2.17 (1H, t, J=3.1 Hz), 2.32 (1H, dd, J=6.6, 3.0 Hz), 2.56 (1H, dd, J=13.5, 5 Hz), 2.58 (1H, s), 4.09 (2H, m), 5.23 (2H, s), 6.42 (1H, bs), 7.28–7.40 (5H, m); MS[ISP] 363 (M+H$^{30}$);

EXAMPLE 20

(1S,2R,3R,5R,6S)-2-Acetylamino-3-hydroxy-3-tritio-bicyclo [3.1.0]hexane-2,6-dicarboxylic acid 2-benzyl ester 6-ethyl ester (XXI) and (1S,2R,3S,5R,6S)-2-Acetylamino-3-hydroxy-3-tritiobicylo[3.1.0] hexane-2,6-dicarboxylic 2-benzyl ester 6-ethyl ester (XXII)

Radiochemical samples were counted in a wallac Win-Spectral 1414 Liquid Scintillation Counter using OptiPhase 'HiSafe'3 as scintillation cocktail.

n-Butyl lithium (200 μL, 0.312 mmol, 1.56 M in n-hexane) and N,N,N',N'-tetramethylethylenediamine (52 μL, 0.347 mmol) were transferred into a 7.5 mL-two-necked-flask mounted to the tritiation apparatus under argon. The stopcock of the side neck was closed and the mixture was stirred under an atmosphere of tritium gas for 2 h 43 min, while the tritium gas pressure dropped from 646 mbar to 559 mbar. Excess tritium gas was reabsorbed onto the uranium bed and the volatile components were lyophilized off. The residue was dried at 10$^{-3}$ mbar for about 5 min. The flask was filled with dry nitrogen and the LiT was suspended in THF (250 μL), which was added by syringe through the silicon septum (Hamilton # 76005) of the side neck. Then trimethylborate (35 μL, 0.314 mmol) was added and the mixture was stirred for 10 min. The two-necked-flask was disconnected from the tritiation apparatus and equipped with a balloon filled with argon. (1S,2R,5R,6S)-2-acetylamino-3-oxo-bicyclo[3.1.0]hexane-2,6-dicarboxylic 2-benzyl ester 6-ethyl ester (XVI) (118.7 mg, 0.33 mmol) in THF (250 μL) was added at −60° C. After stirring for 30 min the reaction was quenched by adding 1 N HCl (0.31 mL). The reaction mixture was partitioned between EtOAc and H$_2$O. The organic phase was washed with saline (1×) and dried over Na$_2$SO$_4$. The total $^3$H-activity of the crude product was 5.18 Ci. Column chromatography using 15 g of Lichroprep Si60 25–40 μm (Merck Art.1.09390) with toluene/acetone 5:1 afforded 1.152 Ci of (1S,2R,3R,5R,6S)-2-acetylamino-3-hydroxy-3-tritio-bicyclo[3.1.0]hexane-2,6-dicarboxylic acid 2-benzyl ester 6-ethyl ester (XXI) with 99% radiochemical purity according to TLC (toluene/acetone 3:1). The specific activity was 23.9 Ci/mmol according to mass spectrometry. In addition about 2 Ci of (1S,2R,3S,5R,6S)-2-acetylamino-3-hydroxy-3-tritio-bicyclo [3.1.0]hexane-2,6-dicarboxylic acid 2-benzyl ester 6-ethyl ester (XXII) were isolated.

EXAMPLE 21

(1S,2R,3R,5R,6S) -2-Amino-3-deutero-3-hydroxy-bicyclo [3.1.0]hexane-2,6-dicarboxylic acid (I-3)

(1S,2R,3R,5R,6S)-2-Acetylamino-3-deutero-3-hydroxy-bicyclo [3.1.0]hexane-2,6-dicarboxylic acid 2-benzyl ester 6-ethyl ester (XIX) (15 mg, 0.058 mmol) was refluxed in 10% HCl (3.7 mL) for 6 h. The solution was cooled to 23° C. and evaporated to dryness. The remaining pale yellow solid was dissolved in EtOH (3 mL) and propylene oxide (1.6 mL) and refluxed for 15 min, whereupon the amino acid precipiated as white fluffy material. After cooling to 23° C., the product was filtered off, washed with ether, taken up in water and lyophilized to give (1S,2R,3R,5R,6S)-2-amino-3-deutero-3-hydroxy-bicyclo[3.1.0]hexane-2,6-dicarboxylic acid (I-3) (12 mg, 71%) as a white solid. Analytical data the same as in example 15.

EXAMPLE 22

(1S,2R,3R,5R,6S)-2-Amino-3-hydroxU-3-tritio-bicyclo [3.1.0]hexane-2,6-dicarboxylic acid (I-5)

(1S,2R,3R,5R,6S)-2-Acetylamino-3-hydroxy-3-tritio-bicyclo [3.1.0]hexane-2,6-dicarboxylic acid 2-benzyl ester 6-ethyl ester (XXI) (576 mCi) was refluxed in 10% HCl (5 mL) for 6 h. The reaction mixture was diluted with H$_2$O (5 mL) and applied onto a Dowex 50WX8 100–200 mesh cation exchange column (7.5×70 mm). The column was rinsed with H$_2$O (20 mL). Elution with 2 N NH$_4$OH (20 mL) afforded (1S,2R,3R,5R,6S)-2-amino-3-hydroxy-3-tritio-bicyclo [3.1.0]hexane-2,6-dicarboxylic acid (I-5) (280 mCi).

The radiochemical purity was 91.7% according to TLC (n-BuOH/HOAc/$H_2O$ 3:1:1). The crude product (56 mCi) was purified by HPLC on a µBondapak C18 column (3.9× 300 mm) using $H_2O$/acetonitrile 95:5 (v/v) as mobile phase with a flow rate of 0.8 mL/min and UV-detection at 220 nm. The total $^3$H-activity obtained was 43 mCi and the radiochemical purity was 98.1% according to TLC (n-BuOH/HOAc/$H_2O$ 3:1:1).

EXAMPLE 23

(1S,2R,3R,5R,6S)-2-Azido-3-methoxy-bicyclo[3.1.0]hexane-2,6-dicarboxylic acid 2-benzyl ester 6-ethyl ester (XXIII-1)

A solution of (1S,2R,3R,5R,6S)-2-azido-3-hydroxybicyclo [3.1.0]hexane-2,6-dicarboxylic acid 2-benzyl ester 6-ethyl ester (VII-1) (345 mg, 1.0 mmol), 2,6-di-tert.-butylpyridine (1.35 mL, 6.0 mmol) and methyl triflate (0.55 mL, 5.0 mmol) in DCM (2 mL) was stirred at 23° C. for 4 d. The reaction mixture was poured on ice, acidified with 1 N HCl and extracted with ether. After washing with sat. $NaHCO_3$-sol., brine and drying over $MgSO_4$ the crude product was purified by silica gel column chromatography with hexane/EtOAc 4:1 to give (1S,2R,3R,5R,6S)-2-azido-3-methoxy-bicyclo[3.1.0]hexane-2,6-dicarboxylic acid 2-benzyl ester 6-ethyl ester (XXIII-1) (226 mg, 63%) as a yellow oil. $^1$H-NMR (250 MHz, $CDCl_3$) □1.26 (3H, t, J=7.1 Hz), 1.77 (1H, t, J=3.5 Hz), 2.05–2.18 (2H, m), 2.25 (1H, dd, J=7, 3.5 Hz), 2.34 (1H, dd, J=12, 7 Hz), 3.28 (3H, s), 3.42 (1H, bt,J=8 Hz), 4.12 (2H, q, J=7.1 Hz), 5.25 (1H, d,J=12 Hz), 5.34 (1H, d, J=12 Hz), 7.30–7.40 (5H, m); MS [EI] 258 [ (M—$CO_2Et-N_2$)$^+$]; □$_D^{20}$–48.02° (c=1.11, $CHCl_3$).

EXAMPLE 24

(1S,2R,3R,5R,6S)-3-Allyloxy-2-azido-bicyclo[3.1.0]hexane-2,6-dicarboxylic acid 2-benzyl ester 6-ethyl ester (XXIII-2)

To a solution of (1S,2R,3R,5R,6S)-2-azido-3-hydroxybicyclo[3.1.0]hexane-2,6-dicarboxylic acid 2-benzyl ester 6-ethyl ester (VII) (200 mg, 0.58 mmol) and allyl 2,2,2-trichloroacetimidate (0.18 mL, 1.16 mmol) in cyclohexane (0.7 mL) was added TfOH (29 □L), whereupon the solution became hot and stirring was continued at 23° C. for 1 h. The reaction mixture was poured on ice, diluted with ether, washed with sat. $NaHCO_3$-sol., brine and dried over $MgSO_4$. The crude product was purified by silica gel column chromatography with hexane/EtOAc 4:1 to give ( 1S,2R, 3R,5R,6S)-3-allyloxy-2-azido-bicyclo [3.1.0]hexane-2,6-dicarboxylic acid 2-benzyl ester 6-ethyl ester (XXIII-2) (31 mg, 14%) as a yellow oil. $^1$H-NMR (250 MHz, $CDCl_3$) □1.26 (3H, t, J=7.1 Hz), 1.76 (1H, t, J=3.5 Hz), 2.03–2.26 (3H, m), 2.32 (1H, dd, J=12, 7 Hz), 3.58 (1H, dd, J=9, 7 Hz), 3.92 (1H, m), 4.02 (1H, m), 4.13 (2H, q, J=7.1 Hz), 5.10–5.22 (2H, m), 5.25 (1H, d,J=12 Hz), 5.34 (1H, d,J=12 Hz), 5.75 (1H, m), 7.30–7.42 (5H, m);MS[EI] 284 [(M-$CO_2Et-N_2$)$^+$]; □$_D^{20}$17.85° (c=0.50, $CHCl_3$).

EXAMPLE 25

(1S,2R,3R,5R,6S)-2-Azido-3-benzyloxy-bicyclo[3.1.0]hexane-2,6-dicarboxylic acid 2-benzyl ester 6-ethyl ester (XXIII-3)

To a solution of (1S,2R,3R,5R,6S)-2-azido-3-hydroxybicyclo [3.1.0]hexane-2,6-dicarboxylic acid 2-benzyl ester 6-ethyl ester (VII) (305 mg, 0.88 mmol) and benzyl 2,2,2-trichloroacetimidate (0.2 mL, 1.06 mmol) in cyclohexane (2.4 mL) and DCM (1.2 mL) was added TfOH (0.05 mL), whereupon the solution became hot and stirring was continued at 23° C. for 5 h. The reaction mixture was poured on ice, diluted with ether, washed with sat. $NaHCO_3$-sol., brine and dried over $MgSO_4$. The crude product was purified by silica gel column chromatography with hexane/EtOAc 4:1 to give (1S,2R,3R,5R,6S)-2-azido-3-benzyloxybicyclo[3.1.0] hexane-2,6-dicarboxylic acid 2-benzyl ester 6-ethyl ester (XXIII-3) (102 mg, 27%) as a yellow oil. $^1$H-NMR (250 MHz, $CDCl_3$) □1.25 (3H, t, J=7.1 Hz), 1.75 (1H, t, J=3.5 Hz), 2.06 (1H, m), 2.17–2.31 (3H, m), 3.60 (1H, bt, J=8 Hz), 4.12 (2H, q, j=7.1 Hz), 4.42 (1H, d, J=12 Hz), 4.57 (1H, d,J=12 Hz), 5.23 (1H, d,J=12 Hz), 5.34 (1H, d,J=12 Hz), 7.15–7.42 (10H, m); MS[ISP] 408 [(M+H-$N_2$)$^+$]; □$_D^{20}$+ 2.03 ° (c=0.99, $CHCl_3$).

EXAMPLE 26

(1S,2R,3R,5R,6S)-3-Allyloxy-2-amino-bicyclo[3.1.0]hexane-2,6-dicarboxylic acid 2-benzyl ester 6-ethyl ester (XXIV-2)

To a solution of (1S,2R,3R,5R,6S)-3-allyloxy-2-azido-bicyclo[3.1.0]hexane-2,6-dicarboxylic acid 2-benzyl ester 6-ethyl ester (XXIII-2) (101 mg, 0.262 mmol) in THF (3.9 mL) and $H_2O$ (0.4 mL) was added $Me_3P$ (0.29 mL, 0.29 mmol, 1 M sol. in THF) and stirring was continued at 23° C. for 3 h. The reaction mixture was diluted with ether, washed with sat. $NaHCO_3$-sol., brine and dried over $Na_2SO_4$. The crude product was purified by silica gel column chromatography with hexane/EtOAc 1:1 (+small amount of $Et_3N$) to give (1S,2R,3R,5R,6S)-3-allyloxy-2-amino-bicyclo[3.1.0] hexane-2,6-dicarboxylic acid 2-benzyl ester 6-ethyl ester (XXIV-2) (47 mg, 50%) as a light brown oil. $^1$H-NMR (250 MHz, $CDCl_3$) □1.24 (3H, t, J=7.1 Hz), 1.76 (1H, t, J=3.5 Hz), 1.93 (2H, bs), 1.99 (1H, m), 2.07–2.18 (2H, m), 2.31 (1H, dd, J=12.5, 7 Hz), 3.45 (1H, bt, J=8 Hz), 3.93 (2H, bd,J=6 Hz), 4.12 (2H, q, J=7.1 Hz), 5.10-5.35 (4H, m), 5.78 (1H, m), 7.28–7.38 (5H, m); MS[ISP] 360 [(M+H)$^+$]; □$_D^{20}$– 10.67° (c=1.00, $CHCl_3$).

EXAMPLE 27

(1S,2R,3R,5R,6S) -2-Amino-3-benzyloxy-bicyclo[3.1.0]hexane-2,6-dicarboxylic acid 2-benzyl ester 6-ethyl ester (XXIV-3)

To a solution of (1S,2R,3R,5R,6S)-2-azido-3-benzyloxy-bicyclo[3.1.0]hexane-2,6-dicarboxylic acid 2-benzyl ester 6-ethyl ester (XXIII-3) (120 mg, 0.276 mmol) in THF (4 mL) and $H_2O$ (0.4 mL) was added $Me_3P$ (0.30 mL, 0.30 mmol, 1 M sol. in THF) and stirring was continued at 23° C. for 4 h. The reaction mixture was diluted with ether, washed with sat. $NaHCO_3$-sol., brine and dried over $Na_2SO_4$. The crude product was purified by silica gel column chromatography with hexane/EtOAc 1:1 (+small amount of $Et_3N$) to give (1S,2R,3R,5R,6S)-2-amino-3-benzyloxy-bicyclo [3.1.0]hexane-2,6-dicarboxylic acid 2-benzyl ester 6-ethyl ester (XXIV-3) (58 mg, 51%) as a yellow oil. $^1$H-NMR (250 MHz, $CDCl_3$) □1.23 (3H, t, J=7.1 Hz), 1.72 (1H, t, J=3.5 Hz), 1.93 (2H, bs), 2.00 (1H, m), 2.10 (1H, dd, J=7, 3.5 Hz), 2.19 (1H, m), 2.27 (1H, dd,J=12,7 Hz), 3.46 (1H, dd,J=8, 7 Hz), 4.10 (2H, q,J=7.1 Hz), 4.47 (2H, s),5.20 (1H,d,J=12 Hz), 5.30 (1H, d,J=12 Hz), 7.18–7.42 (10H,m);MS[ISP] 410 [(M+H)$^+$]; □$_D^{20}$+3.54° (c=0.90, $CHCl_3$).

EXAMPLE 28

(1S,2R,3R,5R,6S)-2-Amino-3-methoxy-bicylo[3.1.0]hexane-2,6-dicarboxylic acid (I-7)

A solution of ( 1S,2R,3R,5R,6S)-2-azido-3-methoxy-bicyclo[3.1.0]hexane-2,6-dicarboxylic acid 2-benzyl ester 6-ethyl ester (XXIII-1) (214 mg, 0.56 mmol) in HOAc (8 mL) and H$_2$O (2 mL) was hydrogenated in the presence of Pd/C (35 mg, 10% Pd/C) at 23° C. for 18 h. The catalyst was removed by filtration, the filter cake washed with 50% aqueous acetic acid. After removal of the solvent in vacuum, the beige residue was refluxed in 10% HCl (15 mL) for 4 h. The solution was cooled to 23° C., filtered, washed with water and evaporated to dryness. The remaining pale yellow solid was dissolved in EtOH (10 mL) and propylene oxide (5.6 mL) and refluxed for 15 min, whereupon the amino acid precipitated. After cooling to 23° C., the product was filtered off, washed with ether and dried to give (1S,2R,3R,5R,6S)-2-amino-3-methoxy-bicyclo [3.1.0]hexane-2,6-dicarboxylic acid (I-7) (100 mg 74%) as a white solid. $^1$H-NMR (250 MHz, D$_2$O) □1.86 (1H, t, J=3.5 Hz), 2.04–2.23 (3H, m), 2.50 (1H, dd, J=12, 7 Hz), 3.29 (3H, s), 3.62 (1H, bt,J=8 Hz); MS[ISN] 214 [(M-H)$^-$]; mp>250° C.; □$_D^{20}$–13.84° (c=1.01, H$_2$O).

EXAMPLE 29 cl (1S,2R,3R,5R,6S)-2-Amino-3-propoxy-bicyclo[3.1.0] hexane-2,6-dicarboxylic acid (I-8)

A solution of (1S,2R,3R,5R,6S)-3-allyloxy-2-azido-bicyclo [3.1.0]hexane-2,6-dicarboxylic acid 2-benzyl ester 6-ethyl ester (XXIII-2) (28 mg, 0.073 mmol) in HOAc (0.75 mL) and H$_2$O (0.25 mL) was hydrogenated in the presence of Pd/C (3 mg, 10% Pd/C) at 23° C. for 18 h. The catalyst was removed by filtration, the filter cake washed with 50% aqueous ethanol. After removal of the solvent in vacuum, the beige residue was refluxed in 10% HCl (1.25 mL) for 4 h. The solution was cooled to 23° C. and evaporated to dryness. The remaining pale yellow solid was dissolved in EtOH (1 mL) and propylene oxide (0.5 mL) and refluxed for 10 min, whereupon the amino acid precipiated. After cooling to 23° C., the product was filtered off, washed with ether and dried to give (1S,2R,3R,5R,6S)-2-amino-3-propoxy-bicyclo [3.1.0]hexane-2,6-dicarboxylic acid (I-8) (13 mg, 72%) as a white solid. $^1$H-NMR (250 MHz, D$_2$O) □0.81 (1H, t, J=7.5 Hz), 1.48 (2H, m), 1.84 (1H, m), 2.16 (3H, m), 2.26 (1H, dd,J=12,7 Hz), 3.43 (2H, m), 3.73 (1H,bt,J=8Hz); MS[ISN] 242 [(M-H)$^-$]; mp >2500 C; □$_D^{20}$3.72° (c=0.19, H$_2$O).

EXAMPLE 30

(1S.2R.3R.5R.6S)-3-Allyloxy-2-amino-bicyclo [3.1.0]hexane-2,6-dicarboxylic acid (I-9)

A solution of (1S,2R,3R,5R,6S)-3-allyloxy-2-amino-bicyclo [3.1.0]hexane-2,6-dicarboxylic acid 2-benzyl ester 6-ethyl ester (XXIV-2) (47 mg, 0.131 mmol) and LiOH.H$_2$O (15 mg, 0.357 mmol) in THF (4 mL), H$_2$O (2 mL) and MeOH (0.4 mL) was stirred at 23° C. for 36 h. The solution was acidified with conc. HCl and evaporated to dryness. The remaining pale yellow solid was suspended in EtOH, filtered, washed with more EtOH and the filtrate was evaporated to dryness. The residue was dissolved in EtOH (1 mL) and propylene oxide (1 mL) and refluxed for 3 min, whereupon the amino acid precipitated. After cooling to 23° C., the product was filtered off, washed with ether and dried to give (1S,2R,3R,5R,6S)-3-allyloxy-2-amino-bicyclo[3.1.0] hexane-2,6-dicarboxylic acid (I-9) (19 mg, 59%) as a white solid. $^1$H-NMR (250 MHz, D$_2$O) □1.48 (1H, t, J=3.5 Hz), 1.78 (2H, m), 1.98 (1H, ddd, J=12.5, 8,3.5 Hz), 2.27 (1H, dd, J=12.5, 7 Hz), 3.44 (1H, bt, J=7.5 Hz), 3.97 (2H, m), 5.13–5.26 (2H, m), 5.82 (1H, ddt, J=18, 11, 6 Hz); MS[ISN] 240 [(M-H)$^-$]; mp>250° C.; Ξ$_D^{20}$–10.62° (c=0.40, H$_2$O).

EXAMPLE 31

(1S,2R,3R,5R,6S)-2-Amino-3-benzyloxy-bicyclo [3.1.0]hexane-2,6-dicarboxylic acid (I-10)

A solution of (1S,2R,3R,5R,6S)-2-amino-3-benzyloxy-bicyclo [3.1.0] hexane-2,6-dicarboxylic acid 2-benzyl ester 6-ethyl ester (XXIV-3) (50 mg, 0.122 mmol) and LiOH.H$_2$O (13 mg, 0.30 mmol) in THF (4 mL), H$_2$O (2 mL) and MeOH (0.4 mL) was stirred at 23° C. for 36 h. The solution was acidified with conc. HCl and evaporated to dryness. The remaining pale yellow solid was suspended in EtOH, filtered, washed with more EtOH and the filtrate was evaporated to dryness. The residue was dissolved in EtOH (1 mL) and propylene oxide (1 mL) and refluxed for 3 min, whereupon the amino acid precipitated. After cooling to 23° C., the product was filtered off, washed with ether and dried to give (1S,2R,3R,5R,6S)-2-amino-3-benzyloxybicyclo[3.1.0] hexane-2,6-dicarboxylic acid (I-10) (26 mg, 72%) as a white solid. $^1$H-NMR (250 MHz, D$_2$O) □1.57 (1H, t, J=3.5 Hz), 1.97 (2H, m), 2.13 (1H, ddd, J=12.5, 8,3.5 Hz), 2.35 (1H, dd, J=12.5, 7 Hz), 3.73 (1H, dd, J=8, 7 Hz), 4.51 (2H, s), 7.36 (5H, bm); MS[ISN] 290 [(M-H)$^-$]; mp>250° C.; □$_D^{20}$– 5.69° (c=0.25, H$_2$O).

EXAMPLE 32

(1S,2R,3R.5R,6S)-2-Azido-3-trifluoromethanesulfonyloxy-bicyclo [3.1.0]hexane-2,6-dicarboxylic acid 2-benzyl ester 6-ethyl ester (XXV)

To a solution of (1S,2R,3R,5R,6S)-2-azido-3-hydroxy-bicyclo[3.1.0]hexane-2,6-dicarboxylic acid 2-benzyl ester 6-ethyl ester (VUI-1) (518 mg, 1.5 mmol) and pyridine (0.36 mL, 4.5 mmol) in DCM (19 mL) at –78° C. was added trifluoromethanesulfonic anhydride (0.37 mL, 2.25 mmol) in DCM (1.4 mL) and the mixture was allowed to reach 0° C. The reaction mixture was diluted with ether, poured on ice, extracted with sat. CuSO$_4$-sol. and brine, followed by drying over Na$_2$SO$_4$. After removal of the solvent in vacuum, the crude product was purified by silica gel column chromatography with hexane/EtOAc 4:1 to give (1S,2R,3R,5R,6S)-2-azido-3-trifluoromethanesulfonyloxy-bicyclo[3.1.0]hexane-2,6-dicarboxylic acid 2-benzyl ester 6-ethyl ester (XXV) (574 mg, 86%) as a colorless oil. $^1$H-NMR (250 MHz, CDCl$_3$) □ 1.27 (3H, t, J=7.1 Hz), 1.84 (1H, t,J=3.5 Hz), 2.17 (1H, m), 2.34 (1H, dd,J=7, 3.5 Hz), 2.53 (2H, m), 4.15 (2H, q,J=7.1 Hz),4.58 (1H,bt,J=8Hz), 5.26 (1H, d,J=2 Hz), 5.41 (1H, d,J=12 Hz), 7.39 (5H, s); MS[ISP] 495 (M+NH$_4^+$); □$_D^{20}$–17.30° (c=1.09, CHCl$_3$).

EXAMPLE 33

(1S,2R,5R,6S)-2-Azido-bicyclo[3.1.0]hex-3-ene-2,6-dicarboxylic acid 2-benzyl ester 6-ethyl ester (XXVI-1)

To a solution of (1S,2R,3R,5R,6S)-2-azido-3-trifluoromethanesulfonyloxy-bicyclo[3.1.0]hexane-2,6-dicarboxylic acid 2-benzyl ester 6-ethyl ester (XXV) (1.36 g, 2.85 mmol) in THF (5.7 mL) was added DBU (0.47 mL, 3.13 mmol) and the mixture was stirred at –50° C. for 3 h. After dilution with ethyl acetate, the solution was washed with 1 N HCl-sol., sat. NaHCO$_3$-sol. and brine, followed by drying over MgSO$_4$. Removal of the solvent in vacuum left the crude (1S,2R,5R,6S)-2-azido-bicyclo[3.1.0]hex-3-ene-2,6-dicarboxylic acid 2-benzyl ester 6-ethyl ester (XXVI) (566 mg, 61%) as a brownish oil, sufficiently pure for further transformations. $^1$H-NMR (250 MHz, CDCl$_3$) □1.27 (3H, t, J=7.1 Hz), 1.76 (1H, t, J=3.5 Hz), 2.59 (1H, dt, J=7, 3.5 Hz), 2.67 (1H, ddd, J=7, 3.5, 2 Hz), 4.14 (2H, q,J=7.1 Hz), 5.27 (2H, s), 5.53 (1H, d, J=5.5 Hz), 6.25 (1H, dd, J=5.5, 2Hz), 7.37 (5H, s); MS[ISP] 345 (M+NH$_4^+$); □$_D^{20}$–7183.54° (c=1.08, CHCl$_3$).

EXAMPLE 34

(1S,2R,5R,6S)-2-Amino-bicyclof[3.1.01]hex-3-ene-2,6-dicarboxylic acid 2-benzyl ester 6-ethyl ester (XXVII)

To a solution of (1S,2R,5R,6S)-2-azido-bicyclo [3.1.0] hex-3-ene-2,6-dicarboxylic acid 2-benzyl ester 6-ethyl ester (XXVI) (66 mg, 0.202 mmol) in THF (4.5 mL) and H$_2$O (0.5 mL) was added polymer supported PPh$_3$ (130 mg, 0.404 mmol, 3.1 mmollg) and the mixture was stirred at 60° C. for 19 h. The resin was filtered off and washed with DCM. Removal of the solvent in vacuum left a yellow oil which was purified by silica gel column chromatography with hexane/ethyl acetate 1:3 to give (1S,2R,5R,6S) -2-amino-bicyclo [3.1.0] hex-3-ene-2,6-dicarboxylic acid 2-benzyl ester 6-ethyl ester (XXVII) (19 mg, 31%) as a colorless oil. $^1$H-NMR (250 MHz, CDCl$_3$) ☐1.25 (3H, t, J=7.2 Hz), 1.55 (1H, t, J=2.9 Hz), 1.78 (2H, bs), 2.53 (2H, m),4.12 (2H, q,J=7.2 Hz), 5.21 (2H, s), 5.37 (1H, d,J=5.3 Hz), 6.07 (1H, dd,J=5.3, 2 Hz), 7.35 (5H, s); MS[ISP] 302 (M+H$^+$); ☐$_D^{20}$–322.98 (c=0.77, CHCl$_3$).

EXAMPLE 35

(1S,2R,5R,6S)-2-Amino-bicyclo [3.1.0]hex-3-ene-2, 6-dicarboxylic acid (I-10)

A solution of (1S,2R,5R,6S)-2-amino-bicyclo[3.1.0]hex-3-ene-2,6-dicarboxylic acid 2-benzyl ester 6-ethyl ester (XXVII) (19 mg, 0.063 mmol) and LiOH.H$_2$O (8 mg, 0.19 mmol) in THF (2 mL), H$_2$O (0.5 mL) and MeOH (0.2 mL) was stirred at 23° C. for 10 h. The solution was acidified with conc. HCl and evaporated to dryness. The remaining pale yellow solid was suspended in EtOH, filtered, washed with more EtOH and the filtrate was evaporated to dryness. The residue was dissolved in EtOH (1 mL) and propylene oxide (1 mL) and refluxed for 3 min, whereupon the amino acid precipiated. After cooling to 23° C., the product was filtered off, washed with ether and dried to give (1S,2R,5R,6S)-2-amino-bicyclo[3.1.0]hex-3-ene-2,6-dicarboxylic acid (I-10) (11 mg, 95%) as a white solid. $^1$H-NMR (250 MHz, D$_2$O) ☐1.59 (1H, t,J=3 Hz), 2.32 (1H, m), 2.60 (1H, m), 5.44 (1H, d, J=5.5 Hz), 6.37 (1H, dd,J=5.5, 2 Hz); MS[ISN] 182 [(M-H)$^-$]; mp>250° C.;

EXAMPLE 36

(1S,2R.5R,6S)-2-Amino-3,4-ditritio-bicyclo [3.1.0] hex-3-ene-2,6-dicarboxylic acid (I-B)

Radiochemical samples were counted in a Berthold BF 5020 liquid scintillation counter using Safetron-150 as scintillation cocktail.

A solution of (1S,2R,5R,6S)-2-amino-bicyclo[3.1.0]hex-3-ene-2,6-dicarboxylic acid (I-10) (4.4 mg, 20 μmol) in EtOH (0.5 mL) and H$_2$O (0.5 mL) was stirred in the presence of Pd/C (1 mg, 10% Pd on activated carbon) under an atmosphere of tritium gas for 1 h at 23° C. Excess tritium gas was reabsorbed onto the uranium bed and the solvent was lyophilized off. The residue was thrice taken up in EtOH (0.5 mL) and H$_2$O (0.5 mL), stirred briefly and lyophilized to ensure complete removal of labile bound tritium. The residue was suspended in EtOH/H$_2$O 1:1 and the catalyst was removed by filtration through a 0.45 μm Millex-HA cartridge. The total activity of the crude product was 718 mCi. The radiochemical purity was 94.3% according to TLC [n-BuOH/HOAc/H$_2$O 3:1:1]. Part of the crude product (72 mCi) was purified by HPLC on a Nucleosil C8 column (5 μm, 4×250 mm), using a 25 mM KH$_2$PO$_4$-sol. as mobile phase with a flow rate of 0.5 mL/min and UV-detection at 220 nm. In order to remove the buffer salt from the mobile phase the sample was applied onto a SP-Sephadex cation exchange column (10× 115 mm, H$^+$-form). The column was rinsed with H$_2$O (20 mL) and the compound was eluted with 2 N NH$_4$OH while 5 min-fractions were collected. Fractions 6 and 7 containing $^3$H-activity were pooled and the volume was reduced to ca. 2 mL by evaporation at ca. 25 mbar. The sample was diluted to 20 ml with EtOH/H$_2$O 1:1. The total activity was 37.5 mCi. The radiochemical purity was 98.3% according to TLC [n-BuOH/HOAc/H$_2$O 3:1:1]. The specific activity determined by mass spectrometry was 35 Ci/mmol.

EXAMPLE 37

(1S,2R,3S,5R,6S)-2,3-Diazido-bicyclo[3.1.0] hexane-2,6-dicarboxylic acid 2-benzyl ester 6-ethyl ester (XXVIII-1)

To a solution of (1S,2R,3R,5R,6S)-2-azido-3-trifluoromethanesulfonyloxybicyclo[3.1.0]hexane-2,6-dicarboxylic acid 2-benzyl ester 6-ethyl ester (XXV) (200 mg, 0.48 mmol) in DMF (0.8 mL) was added NaN$_3$ (187 mg, 2.88 mmol) and the mixture was stirred at 80° C. for 1 h. After cooling to 23° C., the reaction was poured onto ice, extracted with ethyl acetate, washed with brine and dried over MgSO$_4$. Removal of the solvent in vacuum left the crude (1S,2R,3S,5R,6S)-2-diazido-bicyclo [3.1.0] hex-3-ene-2,6-dicarboxylic acid 2-benzyl ester 6-ethyl ester (XXVIII), contaminated with ca. 12% of (1S,2R,5R,6S)-2-azido-bicyclo [3.1.0]hex3-ene-2,6-dicarboxylic acid 2-benzyl ester 6-ethyl ester (XXVI), which was removed by reacting the mixture with OsO$_4$ (3 drops of a 2.5% sol. in t-BuOH), NMO (18 mg, 0.162 mmol) in acetone (1.5 mL) and H$_2$O (3 mL) at 23° C. for 24 h. After quenching with sodium sulfite (ca. 150 mg ) the reaction was poured onto ice, extracted with EtOAc (3×50 mL) and dried over MgSO$_4$. After removal of the solvent in vacuum, the residue was purified by silica gel column chromatography with hexane/ethyl acetate 4:1 to give (1S,2R,3S,5R,6S)-2-diazido-bicyclo[3.1.0]hex-3-ene-2,6-dicarboxylic acid 2-benzyl ester 6-ethyl ester (XXVIII) (81 mg, 49%) as a colorless oil. $^1$H-NMR (250 MHz, CDCl$_3$) ☐1.27 (3H, t, J=7.2 Hz), 1.97 (1H, m), 2.02 (1H, d, J=15.2 Hz), 2.32–2.40 (2H, m), 2.48 (1H, ddd, J=15, 7.5, 5 Hz), 4.14 (2H, q, J=7.2 Hz), 4.20 (1H, d, J=7.4 Hz), 5.28 (2H, s), 7.39 (5H, s); MS[ISP] 388 (M+NH$_4$+); ☐$_D^{20}$56.71° (c=1.11, CHCl$_3$).

EXAMPLE 38

(1S,2R,3S,5R,6S)-2,3-Diamino-bicylo [3.1.0] hexane-2,6-dicarboxylic acid (I-12)

A solution of (1S,2R,3S,5R,6S)-2-diazido-bicyclo[3.1.0] hex-3-ene-2,6-dicarboxylic acid 2-benzyl ester 6-ethyl ester (XXVIII-1) (45 mg, 0.122 mmol) in HOAc (3.8 mL) and H$_2$O (0.95 mL) was hydrogenated in the presence of Pd/C (12 mg, 10% Pd/C) at 23° C. for 18 h. The catalyst was removed by filtration, the filter cake washed with water. After removal of the solvent in vacuum, the brown residue was refluxed in 10% HCl (8.9 mL) for 4 h. The solution was cooled to 23° C., filtered, washed with water and evaporated to dryness. The remaining beige solid was dissolved in EtOH (7.1 mL) and propylene oxide (3.8 mL) and refluxed for 15 min, whereupon the amino acid precipiated. After cooling to 23° C., the product was filtered off, washed with ether and dried to give (1S,2R,3S,5R,6S)-2,3-diamino-bicyclo[3.1.0]hexane-2,6-dicarboxylic acid (I-12) (19 mg, 79%) as a beige solid. $^1$H-NMR (250 MHz, D$_2$O) ☐1.80 (1H, t, J=3 Hz), 2.00 (1H, dd, I=15, 5 Hz), 2.10 (1H, m), 2.15 (1H, dd, I=5,3 Hz), 2.82 (1H, ddd, J=15, 10, 5 Hz), 4.07 (1H, dd, J=10, 5 Hz); MS[ISN]199 [(M-H)$^-$]; mp>250° C.; ☐$_D^{20}$+9.50° (c=0.29, H$_2$O).

What is claimed is:

1. A process for the preparation of a compound of formula

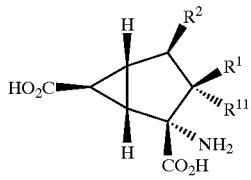

I wherein

R¹ is hydroxy, lower alkoxy, lower alkenyloxy, benzyloxy, hydrogen, deuterium or tritium, R¹¹ is hydrogen, deuterium, tritium, hydroxy or amino, and R² is hydrogen or tritium, or R¹ and R² form a bond, which process comprises:

a) reacting a compound of formula

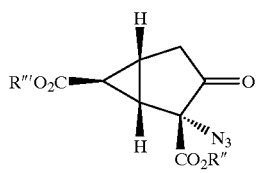

IX with a reducing agent, to obtain a compound of formula VII and a compound of formula X

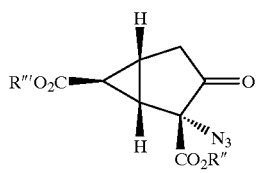

VII

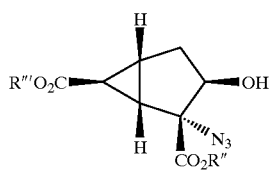

X wherein R''' and R'' are each independently selected from benzyl or lower alkyl, and then, b) reacting with a reducing agent to reduce the azide group, and c) hydrolyzing the ester groups, to obtain a compound of formula I.

2. The process according to claim 1, further comprising, after step a):

d) reacting the compound of formula VII and the compound of formula X with trifluoromethane sulfonic acid to obtain a resultant, and then e) reacting the resultant of step d) in a base to obtain a compound of formula XXVI

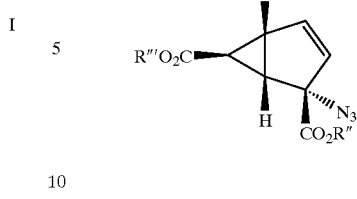

XXVI and f) treating with a gas selected from the group consisting of hydrogen and tritium gas and a mixtures thereof.

3. The process according to claim 1, further comprising, after step a):

d) reacting the compound of formula VII and the compound of formula X with trifluoromethane sulfonic acid to obtain a resultant, and then e) reacting the resultant of step d) with a reagent having an azide group in a polar, aprotic solvent, to obtain a compound of formula XXVIII

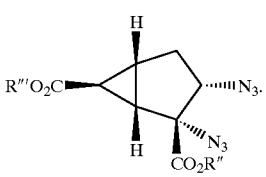

XXVIII

4. The process according to claim 1, further comprising, after step a):

d) alkylating, alkenylating or benzylating the compound of formula VII and the compound of formula X.

5. A process for the preparation of a compound of formula VII

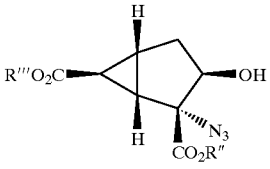

VII wherein R''' and R'' are each independently selected from benzyl or lower alkyl, comprising reacting a compound of formula IX

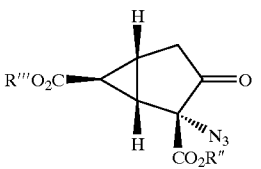

IX with a reducing agent, to obtain a compound of formula VII.

6. A process for the preparation of a compound of formula

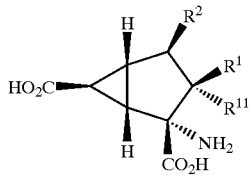

I wherein $R^1$ is hydroxy, lower alkoxy, lower alkenyloxy, benzyloxy, hydrogen, deuterium or tritium, $R^{11}$ is hydrogen, deuterium, tritium, hydroxy or amino, and $R^2$ is hydrogen or tritium, or $R^1$ and $R^2$ form a bond, which process comprises:

a) providing a compound of formula VII,

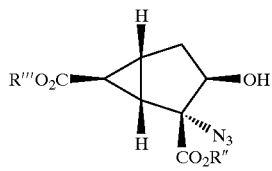

VII wherein R''' and R'' are each independently selected from benzyl or lower alkyl and then, b) reacting with a reducing agent to reduce the azide group, and c) hydrolyzing the ester groups, to obtain a compound of formula I.

7. The process according to claim 6, further comprising, after step a):

d) reacting the compound of formula VII with trifluoromethane sulfonic acid to obtain a resultant, and then e) reacting the resultant of step d) in a base to obtain a compound of formula XXVI

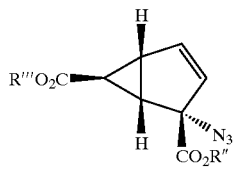

XXVI and f) treating with a gas selected from the group consisting of hydrogen and tritium gas and mixtures thereof.

8. The process according to claim 6, further comprising, after step a):

d) reacting the compound of formula VII with trifluoromethane sulfonic acid anhydride to obtain a resultant, and then e) reacting the resultant of step d) with a reagent having an azide group in a polar, aprotic solvent, to obtain a compound of formula XXVIII

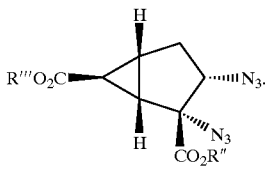

XXVII

9. The process according to claim 6, further comprising, after step a):

d) alkylating, alkenylating or benzylating the compound of formula VII.

10. A process for the preparation of a compound of formula

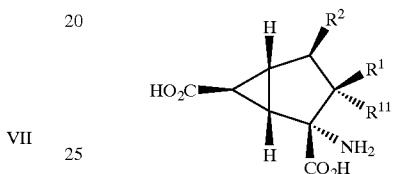

I wherein $R^1$ is hydroxy, lower alkoxy, lower alkenyloxy, benzyloxy, hydrogen, deuterium or tritium, $R^{11}$ is hydrogen, deuterium, tritium, hydroxy or amino, and $R^2$ is hydrogen or tritium, or $R^1$ and $R^2$ form a bond, which process comprises:

a) providing a compound of formula X,

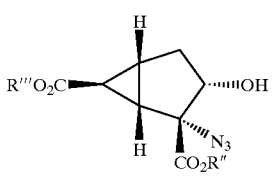

X wherein R''' and R'' are each independently selected from benzyl or lower alkyl and then, b) reacting with a reducing agent to reduce the azide group, and c) hydrolyzing the ester groups, to obtain a compound of formula I.

11. The process according to claim 10, further comprising, after step a):

d) reacting the compound of formula X with trifluoromethane sulfonic acid anhydride to obtain a resultant, and then e) reacting the resultant of step d) in a base to obtain a compound of formula XXVI

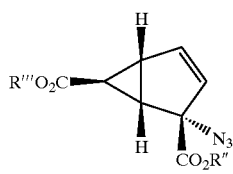

and f) treating with a gas selected from the group consisting of hydrogen and tritium gas and mixtures thereof.

12. The process according to claim 10, further comprising, after step a):

d) reacting the compound of formula X with trifluoromethane sulfonic acid anhydride to obtain a resultant, and then e) reacting the resultant of step d) with a reagent having an azide group in a polar, aprotic solvent, to obtain a compound of formula XXVIII

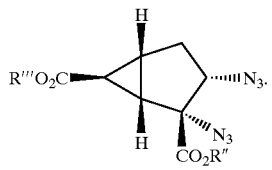

13. The process according to claim 10, further comprising, after step a):

d) alkylating, alkenylating or benzylating the compound of formula X.

14. A compound of formula

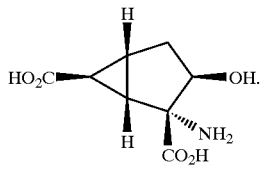

15. A compound of formula

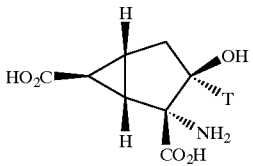

wherein T is tritium.

16. A compound of formula

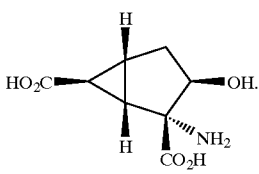

wherein R" and R"" are each independently selected from benzyl or lower alkyl.

17. A method of controlling or preventing a neurological disease or a psychiatric disorder comprising administering to a patient in need of treatment an effective amount of the compound of formula I-A.

18. The method according to claim 17, wherein the dosage is from about 1 mg to about 1000 mg per day.

* * * * *